(12) United States Patent
Clayberger et al.

(10) Patent No.: US 7,745,390 B2
(45) Date of Patent: Jun. 29, 2010

(54) ANTIMICROBIAL PEPTIDES

(75) Inventors: Carol Clayberger, Stanford, CA (US); Alan M. Krensky, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 669 days.

(21) Appl. No.: 11/438,563

(22) Filed: May 22, 2006

(65) Prior Publication Data

US 2006/0287232 A1 Dec. 21, 2006

Related U.S. Application Data

(60) Provisional application No. 60/684,032, filed on May 23, 2005.

(51) Int. Cl.
*A61K 38/16* (2006.01)
(52) U.S. Cl. ............................. 514/2; 514/13; 514/14; 530/324
(58) Field of Classification Search ........................ None
See application file for complete search history.

(56) References Cited

U.S. PATENT DOCUMENTS 6,485,928 B2 * 11/2002 Stenger et al. ................ 435/32

FOREIGN PATENT DOCUMENTS

WO WO 99/22755 5/1999
WO WO 2005/090385 9/2005

OTHER PUBLICATIONS

Wang et. al., J. Immunol., 2000, vol. 165, pp. 1486-1490.*
Zhuo Wang, et al., "Bactericidal and Tumoricidal Activities of Synthetic Peptides Derived from Granulysin," *The Journal of Immunology*, 2000, 165: 1486-1490.
Anmei Deng, et al., "Granulysin, a Cytolytic Molecule, Is Also a Chemoattractant and proinflammatory activator," *The Journal of Immunology*, 2005, 174: 5243-5248.
William A. Ernst, et al., "Granulysin, a T Cell Product, Kills bacteria by Altering Membrane Permeability" *The Journal of Immunology*, 2000, 165: 7102-7108.
Alan M. Krensky, et al., "Granulysin: A Novel Host Defense Molecule," *American Journal of Transplantation*, Aug. 2005, 5: 1789-1792.
Qing LI, et al., "Hemolysis of Erythrocytes by Granulysin-Derived Peptides but Not by Granulysin," *Antimicrobial Agents and Chemotherapy*, Jan. 2005, vol. 49, No. 1, 388-397.
Ayyalusamy Ramamoorthy, et al., "Cell selectivity correlates with membrane-specific interactions: A case study on the antimicrobial peptide G15 derived from granulysin," *Biochimica et Biophysica Acta* 1758:154-163, Mar. 2006.

* cited by examiner

*Primary Examiner*—Christopher R. Tate
*Assistant Examiner*—Roy Teller
(74) *Attorney, Agent, or Firm*—David J. Aston; Peters Verny, LLP

(57) ABSTRACT

Artificial antimicrobial peptides are obtained by alterations in alpha helical portions of a known antimicrobial protein, granulysin. The peptides obtained have significantly improved antimicrobial activity and lack the ability to lyse mammalian cells, which may be toxic to a host. The peptides may be designed according to certain guidelines, and may further be modified by the addition of altered residues and alterations in normal peptide secondary and tertiary structure, including modifications in quaternary (multimeric) structure.

23 Claims, 5 Drawing Sheets

Representative results of lysis of *E. coli* are shown below.

1A

The microtiter plate MIC assay in media containing different concentrations of NaCl (below). Peptide G8 (left panel) Peptide G9 (center panel) Peptide G5 (right panel)

1B

1C

1D

Effect of G12.21 in controlling *Vibrio cholerae* in vivo ($10^6$ CFU/mouse)

ANTIMICROBIAL PEPTIDES

CROSS-REFERENCE TO RELATED APPLICATIONS

This application claims priority from U.S. Provisional Patent Application No. 60/684,032 filed on May 23, 2005, which is hereby incorporated by reference in its entirety.

STATEMENT OF GOVERNMENTAL SUPPORT

This invention was made during work supported by U.S. National Institutes of Health under grant numbers U19AI056548 and R01AI43348. The government has certain rights in this invention.

REFERENCE TO SEQUENCE LISTING, COMPUTER PROGRAM, OR COMPACT DISK

Applicants assert that the paper copy of the Sequence Listing is identical to the Sequence Listing in computer readable form found on the accompanying computer disk. Applicants incorporate the contents of the sequence listing by reference in its entirety.

BACKGROUND OF THE INVENTION

1. Field of the Invention

The present invention relates to the field of antimicrobial peptides.

2. Related Art

Background

Granulysin, a protein expressed by human cytotoxic T lymphocytes (CTL) and natural killer cells, was discovered in 1987 by Drs. Krensky and Clayberger during a search for genes expressed late (3-5 days) after T cell activation. Granulysin has potent lytic activity against both Gram-negative and Gram-positive bacteria and fungi, including *Mycobacterium tuberculosis* (Mtb), *Salmonella typhimurium*, *Escherichia coli*, *Staphlococcus aureus*, *Cryptococcus neoformus*, *Leishmania major*, *Leishmania monocytogenes*, *Candida albicans*, *Pseudomonas aeruginosa*, and *Vibrio cholera*.

Granulysin is a member of the saposin-like protein (SAP-LIP) family that has been highly conserved for almost one billion years in various organisms. This family includes NK-lysin, a lytic molecule isolated from pig intestine; amoebapores, used by amoebae to kill bacterial invaders, and saposins. Naturally occurring granulysin is a 15 kD molecule which is processed intracellularly to a 9 kD protein. It consists of five alpha helices separated by short loop regions and four cysteine residues that form two intramolecular disulfide bonds. Similar to many other cationic peptides, granulysin lyses both microbes and mammalian cells.

Granulysin plays a central role in the human cellular immune response. T lymphocytes use granulysin to kill both extracellular and intracellular *Mycobacterium tuberculosis*, although the latter also requires perforin. Similarly, exocytosis of granulysin by CTL is required for killing of the fungus *Cryptococcus* as well as *Plasmodium falciparum*, the parasite that causes malaria. Granulysin expressing T cells were detected in cutaneous leprosy lesions at a six fold greater frequency in patients with the localized tuberculoid form as compared with the disseminated lepromatous form of the disease, strongly implicating granulysin in controlling the spread of leprosy. In contrast, perforin was expressed at similar frequencies in both types of leprosy. Although granulysin is apparently not lytic against either HIV or varicella-zoster virus, granulysin killed intracellular varicella virions and accelerated death of varicella infected cells. A study from a Japanese group reported that NK cells from cancer patients with a poor prognosis contained significantly less granulysin than NK cells from cancer patients with a good prognosis or from healthy donors. The levels of perforin were similar in cells from all three groups. In renal transplant recipients, elevated levels of granulysin in both PBL and renal biopsies are associated with acute rejection and poor graft outcome.

Stenger et al. U.S. Pat. No. 6,485,928 describes the use of granulysin as an antimicrobial agent. It further gives the sequence of human granulysin, which may also be found in GenBank Accession number AAN99767, defined herein as a "human granulysin sequence,"

```
                                          (SEQ ID NO: 1)
   MATWALLLLA AMLLGNPGLE VSVSPKGKNT SGRESGFGWA

IWMEGLVFSR LSPEYYDLAR AHLRDEEKSC PCLAQEGPQG

DLLTKTQELG RDYRTCLTIV QKLKKMVDKP T /1/ QRSV

SNAAT RVCRT /2/ GRSRW /3/ RDVCRNFMRR /4/ YQ

SRVIQGLV /5/ AGETAQQICE DLRLCIPSTG PL
```

The H3 region is underlined and is shown again in Table 1, which also indicates alignments with "wild type," or "parent," i.e., non-mutated, sequences, of peptides further developed and tested as described below. As will be discussed below, the inserted numbers, /1/ through /5/, indicate the portions of granulysin from which the present peptides were originally obtained.

Bair U.S. Pat. No. 4,999,369 sets forth the nucleotide and predicted amino acid sequence of the "519" protein, referred to presently as granulysin. The amino acid sequences disclosed include two variants, having aa 16-145 and aa 16-172 of sequence id's no. 3 and 4 of the '928 patent. The '928 patent also discloses that the granulysin polypeptide may be modified with substitutions, insertions or deletions. These sequences may be used to modify or extend the peptides disclosed below.

Wang et al., "Bacterial and Tumoricidal Activities of Synthetic Peptides Derived from Granulysin," J. Immunol. 165: 1486-1490 (2000) discloses a number of synthetic peptides derived from granulysin. These peptides are derived from full-length granulysin and are intended to cover certain predicted alpha helices in granulysin. The authors termed their peptides G1 to G15. Certain substitutions were made in several of the peptides. C→S substitutions were made for each granulysin cysteine. These substitutions disrupted disulfide linkages in the peptide. The authors reported that both G8 (which does not contain C→S substitutions) and G9 (which does contain C→S substitutions) have the same bacterial lysing ability as full-length granulysin. Certain R→Q substitutions were also made in order to study the effects of positively charged residues on lysis. Positively charged residues were reported to be important for lytic activity.

BRIEF SUMMARY OF THE INVENTION

The methods and materials of the present invention are based on the inventors' findings that the antimicrobial activity of native granulysin and granulysin peptides can be improved to a surprising degree by selected, non-natural modifications.

The artificial peptides described here retain certain properties of granulysin, which is particularly attractive as an antimicrobial immunotherapeutic for the following reasons: 1) it is one of only a few cationic peptides of human origin; 2) it rapidly kills a broad spectrum of microbes; 3) it kills both extracellular and intracellular bacteria; 4) the present panel of synthetic peptides based on the granulysin sequence exhibit high activity towards microbes with little or no effect on mammalian cells; 5) certain peptides derived from granulysin are active in high ionic strength (physiological) conditions; 6) a large body of data on the mechanism by which granulysin and its peptides lyse mammalian cells is available; 7) recombinant granulysin can be expressed in *E. coli*; and 8) the sequence of granulysin (or its peptides or the present artificial peptides) is not homologous to any previously studied cationic peptides. At the same time, it has been found that improvements can be made to native granulysin subsequences. That is, by "artificial," it is meant that the peptide sequence does not occur in granulysin or other antimicrobial protein, i.e., it has at least one non-identical residue when compared to a native sequence, as exemplified below.

In one aspect, the present invention comprises individual, dendritic, or multimers of artificial antimicrobial peptide having between 10 and 30 D- or L-amino acid residues in a sequence represented by SEQ ID NO: 2, said peptide sequence having at least 50% sequence identity thereto, and an MIC against at least one of pathogenic bacterium selected from the group consisting of *E. coli*, *S. typhimurium* and *B. cereus* of less than 10 µM; and having minimal lytic activity against mammalian cells. The 50% sequence identity is illustrated by a Table below using as an example G12.26. Various peptides may have other sequence identities, depending on the reference sequence used. The 50% figure is approximate, and may be less, in accordance with the teachings below. In one aspect, the present invention comprises a peptide which has at least 90% sequence identity to peptide G11.46, G12.21 or G14.15, insofar as these peptides are exemplified below as having desirable properties. Along these lines, the peptide may be said to comprise the sequence arg-arg-val-ser-arg-arg (SEQ ID NO: 92), as bolded in the sequence of G12.21, below.

The present artificial antimicrobial peptides may be comprised in a variety of pharmaceutically acceptable compositions, such as a topical formulation or a sterile lyophilized powder for injection, or an oral formulation.

In certain aspects, the invention includes an antimicrobial peptide designed according to guidelines taught below. The peptide may have a net positive charge of at least 8. It may have more D-amino acids than L-amino acids, and/or at least 3 hydrophobic residues, and/or it may comprise at least 7 arg residues. Also, it may have a selected number of charged (positive or negative) residues to be at least 8 residues.

Other activity criteria are also relevant. The peptide may have a MIC (µM) in at least two microbial organisms selected from the group consisting of: *E. coli*, *S. typhimurium*, *V. cholerae* and *B. cereus* of less than about 2.0, and further, it should have minimal lysis of mammalian cells.

BRIEF DESCRIPTION OF THE DRAWINGS

FIG. 2 is a pair of bar graphs (2A and 2B) showing the effect of peptide G12.21 on *V. cholerae* infection in vivo;

DETAILED DESCRIPTION OF THE PREFERRED EMBODIMENT

Sequence Notations

Figure 1:
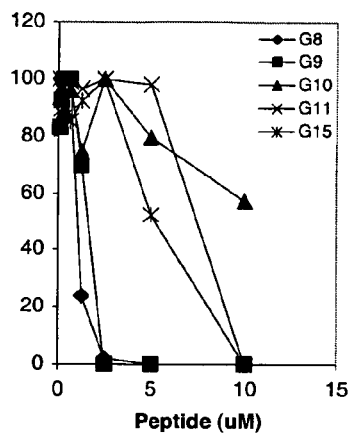
FIGS. 1A-D is a series of graphs showing activity of the present peptides against *E. coli* in different salt concentrations, where 1A shows results of lysis of *E coli*; 1B shows MIC assay in media containing different concentrations of NaCl, with G8 in 1B, G9 in center panel; and G5 in 1D.
Figure 1:
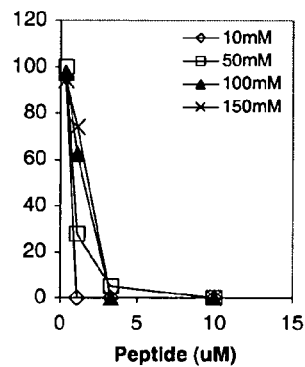
Figure 1:
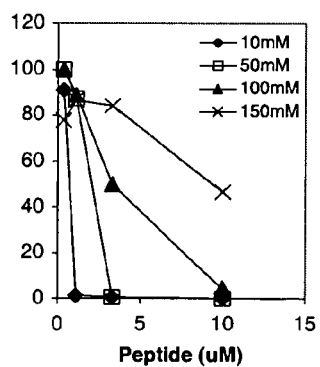
Figure 1:
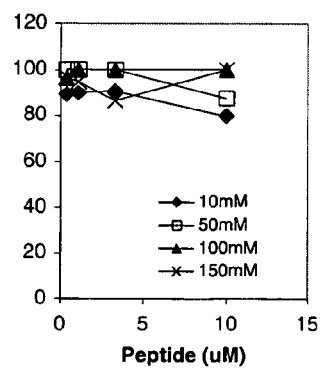

SEQ ID NO: 2 is a subsequence of human granulysin:

1/ QRSVSNAAT RVCRT /2/ GRSRW /3/ <u>RDVCRNFMRR</u> /4/ YQSRVIQGLV /5/

Helix 3 is underlined. As can be seen by matching the sequences given in Table 2:

G8 extends from 1 to 2-4;
G11 extends from 3 to 4;
G12 extends from 3 to 5;
G13 extends from 1 to 3;
G14 extends from 2 to 4;
G20 extends from 2 to 5; and
G21 extends from 1 to 5.

The peptide sequences given here are in standard single letter amino acid designation, using capital letters (IUPAC-IUB Commission on Biochemical Nomenclature (CBN), A One-Letter Notation for Amino Acid Sequences, 1968, Arch. Biochem. Biophys. 125(3), i-v (1968). Lower case letters indicate D-amino acids. Various underlining and bold designations are explained in the text.

The standard single letter and three letter codes for amino acids are used herein and are as follows:

| | | |
|---|---|---|
| A (Ala) Alanine | C (Cys) Cysteine | D (Asp) Aspartic acid |
| E (Glu) Glutamic acid | F (Phe) Phenylalanine | G (Gly) Glycine |
| H (His) Histidine | I (Ile) Isoleucine | K (Lys) Lysine |
| L (Leu) Leucine | M (Met) Methionine | N (Asn) Asparagine |
| P (Pro) Proline | Q (Gln) Glutamine | R (Arg) Arginine |
| S (Ser) Serine | T (Thr) Threonine | V (Val) Valine |
| W (Trp) Tryptophan | Y (Tyr) Tyrosine | |

Initial Studies

The previously published results (Wang et al., supra) showed that only peptides corresponding to the central region of granulysin lysed Jurkat and *S. typhimurium*. Additional peptides were designed based on the predicted secondary structure of granulysin. These are described in Table I, below.

A number of granulysin peptides derived from the granulysin region incorporating predicted Helices H2, H3 and H4 are shown below in Table 1. Residues in bold are changed from the native sequence; lower case indicates D-amino acids; helices from native granulysin are shown in boxes. Peptides G8-G15 were published in Wang et al.

TABLE 1

(SEQ ID NOS 3-7 disclosed respectively, in order of appearance)

| | | | | | |
|---|---|---|---|---|---|
| Granulysin | QRSVSNAATRVCRT | GRSRW | RDVCRNFMRR | Y | QSRVIQGLV |
| | H2 | | H3 | | H4 |
| G8 (23-51) | QRSVSNAATRVCRT | GRSRW | RDVCRNFMRR | | |
| G10 (23-36) | QRSVSNAATRVCRT | | | | |
| G11 (42-51) | | | RDVCRNFMRR | | QSRVIQGLV |
| G12 (42-61) | | | RDVCRNFMRR | Y | |
| G13 (23-41) | QRSVSNAATRVCRT | GRSRW | | | |
| G14 (37-51) | | GRSRW | RDVCRNFMRR | | |
| G15 (37-51, R38, 40→Q38, 40) | | GQSQW | RDVCRNFMRR | | |
| G16 (23→41, A30 → a30) | QRSVSNAaTRVCRT | GRSRW | | | |
| G17 (23-41, A30 → a30, R38, 40 → Q38, 40) | QRSVSNAaTRVCRT | GQSQW | | | |
| G18 (37-51, R46→r46) | | GRSRW | RDVCrNFMRR | | |
| G19 (37-51, R38, 40→Q38, 40, R46→r46) | | GQSQW | RDVCrNFMRR | | |

To further investigate the contribution of secondary structure to function, additional Peptides G16-G19 (beyond peptides G1-G15, previously reported) were synthesized. Peptide G16 is identical to G13, except that a D-alanine residue was substituted for the L-alanine at position 30. G16 lyses bacteria as efficiently as G13, indicating that disruption of the alpha helix does not affect its antimicrobial activity. In peptide G17, the two arginine residues in loop two are substituted with glutamine. This peptide no longer exhibits activity against S. typhimurium. Neither peptide G16 nor G17 lysed Jurkat cells in an appreciable way. The results for G16 suggest that the present peptides may be modified by substitution of a D-alanine in one or two residues without loss of activity.

The results for Peptide G14, consisting of Loop 2/Helix 3, lyses both bacteria and mammalian cells. As shown above, substitution of the two arginine residues in Loop 2 with glutamine abrogates activity against Jurkat cells but only slightly affects lysis of S. typhimurium. Peptide G18 is identical to G14 except that a D-arginine was substituted at position 46. This peptide is indistinguishable from G14 in lysis of S. typhimurium, but loses some activity against Jurkat cells. That is, it does not lyse the cells to the same extent. Peptide G19 incorporates both the R→Q substitutions as well as the D-arginine at position 46. This triple substituted peptide behaves identically to G115, demonstrating again that disruption of the helix does not affect lysis of bacteria.

Methodology

Multiwell Plate Assay

The experiments described above characterizing the activity of granulysin peptides G1-G18 relied on counting bacterial colonies on plates. This assay is quite labor intensive and would not allow evaluation of many different compounds on a number of different microbes. Therefore, we optimized an assay in which the entire procedure could be completed in a single microtiter well. Briefly, peptides are diluted in 10 mM phosphate buffer, pH 7.2 supplemented with 0.03% LB (J. Sambrook, D. W. Russell, Molecular Cloning: A Laboratory Manual (Cold Spring Harbor Laboratory Press, New York, ed. 3, 2001) pg. A2.2, Retrieved from http://openwetware.org/wiki/LB) and 25 µl is added to microtiter wells. Bacteria (25 µl) are added (~5×10$^6$ colony forming units/ml) in the same buffer. After a 3-hour incubation at 37° C., 150 µl of LB is added and the plates are incubated overnight. The OD at 600 nm is read on an ELISA plate reader. The minimum inhibitory concentration (MIC) is the lowest concentration allowing no bacterial growth. The IC$_{50}$ is the concentration of peptide that results in 50% growth compared to the medium. Representative results of lysis of E. coli are shown in FIG. 1. This assay was used to obtain the results listed in Table 2.

Colony Forming Unit (CFU) Assay

The CFU assay is the "gold standard" for evaluating antibiotics. Briefly, bacteria are grown overnight in rich medium, such as LB, and then diluted and grown in log phase for 2-4 hours. Cultures are set up as above, with the initial culture media being 10 mM phosphate buffer/0.03% LB; DMEM or RPMI; or DMEM or RPMI plus 10% serum (fetal calf, human, or mouse). After various periods of time, but generally 3 hours or less, aliquots are removed, diluted in LB at various dilutions, and plated on LB agar plates. Plates are incubated overnight at 37° C. and counted on an automatic colony counter.

Effect of Salt and Serum Concentration

The activity of many cationic antimicrobial peptides is abrogated in isotonic media, most likely because the electrostatic interaction of the positively charged peptides with the negatively charged membrane is disrupted by salt. We reported that recombinant granulysin is most active in low ionic strength media (10 mM) and completely loses activity in media>50 mM salt. To test the effect of ionic strength on granulysin peptides, we repeated the microtiter plate MIC assay in media containing different concentrations of NaCl (FIG. 1B-D). Peptide G8 (left panel) lost minimal activity when the salt concentration was increased from 10 mM to 150 mM. Peptide G9 (center panel), which is identical to G8 except for two cysteine→serine substitutions, was moderately affected by increasing concentrations of salt, confirming a stabilizing effect of the disulfide bonds. Peptide G5 (right panel) was included as a negative control.

Tests were conducted in low salt concentrations so that active peptide candidates could be identified more readily. It is important for in vivo applications that the present antimicrobial peptides be active in physiological salt concentrations (150 mM) as well as in the presence of other tissue components, such as blood plasma (serum). Serum may contain proteases that destroy peptides; the use of D-amino acids can improve protease resistance. See G12.21. A number of the present peptides have been shown to be active in such conditions, in particular G12.12. G8.8, 8.11 have been shown to be active in serum containing media (10% FCS in DMEM or RPMI), whereas the native sequence G8 was not. Also active were G11.6, G11.26, G11.29, G11.30, G11.34, G11.35, G12.11, G12.19, G12.20 and G12.21.

Table 3 shows the results from a number of peptides that were active at 40 µM in serum containing medium (either DMEM or RPMI). For designing analogues of the present sequences, as taught herein, the Table also presents data on the degree of helicity of the active peptides, as measured by circular dichroism. It should be noted that a number of the active peptides listed in the figure are not alpha helices at all. At least one peptide tested was considered to be a random coil, with no detectable secondary structure evident in the circular dichroism measurement.

Design and Evaluation of Additional Derivative Peptides

The observations described above show that introduction of D-amino acids or replacement of cysteine residues with serine (C→S) resulted in peptides that no longer lysed mammalian cells. We now describe additional peptides and their activity. The peptides have been designed, synthesized, and have been tested for lysis of *E. coli* and *S. typhimurium* (gram negative bacteria), *B. cereus* (gram positive bacterium). Results are shown in Table 2 along with the amino acid sequence of the peptide. Changes from the naturally occurring sequence are underlined. In general, the desired result is lysis of bacteria at low concentration (<1 μM).

In the column "Active in DMEM", a blank means no activity. MAP stands for multiple antigenic peptide, where a number of identical peptide chains are synthesized and joined to a common core (like a dendrimer).

TABLE 2

| Peptide Name | *E. coli* DH5a IC50 (μM) | MIC (μM) | *Salmonella* IC50 (μM) | MIC (μM) | *B. cereus* IC50 (μM) | MIC (μM) | Sequence | Active in DMEM |
|---|---|---|---|---|---|---|---|---|
| G8 | 0.55 | 0.75 | 0.89 | 1.4 | 0.9 | 1.4 | QRSVSNAATRVCRTGRSRWRDVCRNFMRR (SEQ ID NO: 8) | |
| G8.1 | 0.55 | 0.75 | 1.75 | 2.8 | 1.75 | 2.8 | QRSVSNAATRVSRTGRSRWRDVSRNFMRR (SEQ ID NO: 9) | |
| G8.16 | 0.4 | 0.7 | >10 | >10 | 7.3 | >10 | QRSVSNPPTRVSRPPRSRWRDVSRPPMRR (SEQ ID NO: 10) | |
| G8.17 | 0.3 | 0.7 | 0.8 | 1.38 | 1.75 | 2.8 | qrsvsnaatrvsrtgrsrwrdvsrnfmrr (SEQ ID NO: 9) | |
| G8.2 | 0.58 | 1.4 | 0.55 | 1.4 | 0.51 | 1.39 | QRSVSRAATRVSRTGRSRWRDVSRNFMRR (SEQ ID NO: 11) | |
| G8.3 | 0.55 | 0.7 | 0.45 | 0.67 | 0.7 | 1.25 | QRSVSNAATRVSRTGRSRWRDVSRRFMRR (SEQ ID NO: 12) | |
| G8.15 | 0.45 | 0.8 | 0.41 | 0.7 | 0.45 | 0.7 | QRSVSRAATRVSRTGRSNWRDVGRRFMRR (SEQ ID NO: 13) | |
| G8.4 | 0.45 | 0.7 | 0.21 | 0.35 | 0.45 | 0.7 | QRSVSRAATRVSRTGRSRWRDVSRRFMRR (SEQ ID NO: 14) | |
| G8.5 | 0.88 | 1.4 | 0.42 | 0.7 | 0.88 | 1.4 | QRAVARAATRVARTGRARWRDVARNFMRR (SEQ ID NO: 15) | |
| G8.6 | 0.45 | 0.7 | 0.43 | 0.7 | 0.89 | 1.5 | QRAVANAATRVARTGRARWRDVARRFMRR (SEQ ID NO: 16) | YES |
| G8.7 | 0.85 | 1.4 | 0.42 | 0.7 | 0.45 | 0.7 | QRAVARAATRVARTGRARWRDVARRFMRR (SEQ ID NO: 17) | |
| G8.8 | 0.21 | 0.35 | 0.42 | 0.7 | 1.7 | 2.5 | QRSVSRaaTRVSRTGRSRWRDVSrrFMRR | YES |
| G8.11 | 0.21 | 0.35 | 0.22 | 0.35 | 0.45 | 0.75 | QRSVSRPPTRVSRTGRSRWRDVSrrFMRR (SEQ ID NO: 18) | YES |
| G8.12 | 0.21 | 0.35 | 0.21 | 0.35 | 0.21 | 0.35 | QRSVSRPPTRVSRTGRSRWRDVSRRFMRR (SEQ ID NO: 18) | |
| G8.9 | 0.45 | 0.7 | 0.22 | 0.35 | 0.45 | 0.7 | QRSVSRAATRVSRTGRSRWRRVSRRFMRR (SEQ ID NO: 19) | YES |
| G8.10 | 0.45 | 0.63 | 0.21 | 0.35 | 0.45 | 0.75 | QRAVARAATRVARTGRARWRRVARRFMRR (SEQ ID NO: 20) | YES |
| G10 | >10 | >10 | >10 | >10 | >10 | >10 | QRSVSNAATRVCRT (SEQ ID NO: 3) | |
| G11 | >10 | >10 | >10 | >10 | >10 | >10 | RDVCRNFMRR (SEQ ID NO: 6) | |
| G11.36 | 0.45 | 0.7 | 0.89 | 1.38 | 0.41 | 0.7 | WRDVSRNFMRRGRSRGWRDVSRNFMRR (SEQ ID NO: 21) | |
| G11.6 | 0.45 | 0.7 | 0.89 | 1.4 | 0.89 | 2.4 | RDVSRRFMRRGSRDVSRRFMRR (SEQ ID NO: 22) | YES |
| G11.26 | 0.4 | 0.7 | 0.21 | 0.35 | 0.21 | 0.35 | RDVSRRFMRRGSRDVSRRFMRRGSRDVSRRFMRR (SEQ ID NO: 23) | YES |
| G11.38 | 0.42 | 0.7 | 0.82 | 1.35 | 0.89 | 1.4 | RDVSRRFMRRGRDVSRRFMRR (SEQ ID NO: 24) | |
| G11.39 | 0.22 | 0.7 | 1.7 | 2.75 | 0.45 | 0.7 | RDVSRRFMRRRDVSRRFMRR (SEQ ID NO: 25) | |
| G11.3 | 1.76 | 2.85 | >10 | >10 | 7.7 | >10 | RRVSRRFMRR (SEQ ID NO: 26) | |
| G11.16 | 0.8 | 1.4 | 3.45 | 5.6 | 7.7 | >10 | RRVVRRFMRR (SEQ ID NO: 27) | |
| G11.18 | 3.4 | 5.65 | 0.88 | 1.4 | 3.51 | 5.7 | RRV-Chg-RRFMRR (SEQ ID NO: 28) | |
| G11.19 | 7.45 | >10 | 7.69 | >10 | 3.41 | 6.65 | RRVVRRLLRR (SEQ ID NO: 29) | |
| G11.20 | 7.7 | >10 | 7.69 | >10 | >10 | >10 | RRLLRRLLRR (SEQ ID NO: 30) | |

TABLE 2-continued

| Peptide Name | E. coli DH5a IC50 (μM) | E. coli DH5a MIC (μM) | Salmonella IC50 (μM) | Salmonella MIC (μM) | B. cereus IC50 (μM) | B. cereus MIC (μM) | Sequence | Active in DMEM |
|---|---|---|---|---|---|---|---|---|
| G11.23 | 0.45 | 0.7 | 0.45 | 0.71 | 0.41 | 0.7 | RRLLRRLLRRGSRRLLRRLLRR (SEQ ID NO: 31) | YES |
| G11.7 | 0.21 | 0.35 | 0.21 | 0.35 | 0.21 | 0.35 | RRVSRRFMRRGSRRVSRRFMRR (SEQ ID NO: 32) | YES |
| G11.8 | >10 | >10 | >10 | >10 | >10 | >10 | KKVSKKFMKK (SEQ ID NO: 33) | |
| G11.15 | 0.8 | 1.38 | 0.41 | 0.7 | 5.85 | >10 | KKVSKKFMKKGSKKVSKKFMKK (SEQ ID NO: 34) | |
| G11.25 | 0.1 | 0.15 | 0.1 | 0.15 | 0.1 | 0.15 | KKVSKKFMKKGSKKVSKKFMKKGSKKVSKKFMKK (SEQ ID NO: 35) | YES |
| G11.55 | 0.98 | 4 | >10 | >10 | 0.1 | 0.2 | kkvskkfmkkgskkvskkfmkkgskkvskkfmkk (SEQ ID NO: 35) | |
| G11.54 | 8.25 | >10 | >10 | >10 | 0.21 | 0.35 | kkvskkfmkkgskkvskkfmkk | |
| G11.10 | 0.21 | 0.35 | 0.21 | 0.35 | 0.21 | 0.35 | RRVSRRFMRRGSRRVSRRFMRRGSRRVSRRFMRR (SEQ ID NO: 36) | YES |
| G11.11 | 7.45 | >10 | >10 | >10 | >10 | >10 | RRDSRRFMRR (SEQ ID NO: 37) | |
| G11.24 | 0.85 | 1.4 | 0.85 | 1.4 | >10 | >10 | rrvsrrfmrr | |
| G11.29 CYC | 0.75 | 1.4 | 1.75 | 2.8 | 0.89 | 1.39 | CRRVSRRFMRRC (SEQ ID NO: 38) | YES |
| G11.30 CYC | 3.5 | 5.7 | 7.7 | >10 | 7.55 | >10 | RRVSRRFMRRD (SEQ ID NO: 39) | |
| G11.31 CYC | 0.42 | 0.61 | 0.41 | 0.7 | 0.4 | 0.7 | CKKVSKKFMKKGSKKVSKKFMKKC (SEQ ID NO: 40) | |
| G11.32 CYC | 0.2 | 0.35 | 0.21 | 0.35 | 0.21 | 0.35 | KKVSKKFMKKGSKKVSKKFMKKD (SEQ ID NO: 41) | YES |
| G11.48 | 2.1 | >10 | >10 | >10 | 3.55 | 5.7 | RRMFRRSVRRCCRRVSRRFMRR (SEQ ID NO: 42) | |
| G11.34 | 0.41 | 0.7 | 1.6 | 2.8 | >10 | >10 | RrvSrrFMrR (SEQ ID NO: 26) | YES |
| G11.45 | >10 | >10 | >10 | >10 | >10 | >10 | RrvSrrFMrRD | |
| G11.35 | 0.41 | 0.7 | 3.25 | 5.7 | >10 | >10 | RRvSrrFmRR (SEQ ID NO: 48) | YES |
| G11.37 | 0.45 | 2.4 | 1.68 | 2.9 | >10 | >10 | RRPSRRFPRR (SEQ ID NO: 43) | |
| G11.40 | 3.28 | >10 | >10 | >10 | >10 | >10 | RRVSRRFMRRSGSGSGSGQQMVQQSGQQFS (SEQ ID NO: 44) | |
| G11.41 | 0.96 | 3.5 | 3.25 | 5.6 | 0.89 | 1.38 | RRVSRRFMRRSRWARKGSGQMVQQSSQQFQ (SEQ ID NO: 45) | |
| G11.42 | 0.21 | 0.35 | 1.35 | 2.8 | 0.11 | 0.4 | VHKRRVSRRFMRRLGH (SEQ ID NO: 46) | |
| G11.43 | 0.42 | 0.75 | 3 | >10 | 0.21 | 0.75 | FDTPRRVSRRFMRRLGH (SEQ ID NO: 47) | |
| G11.44 | 0.21 | 0.38 | 3.15 | 5.75 | 7.7 | >10 | RRVSRRFMRR (SEQ ID NO: 48) | |
| G11.46 | 0.1 | 0.8 | 0.21 | 0.7 | 0.2 | 0.35 | rrrrrrrrVSrrFMrr (SEQ ID NO: 93) | |
| G11.47 | 0.1 | 0.18 | 0.15 | 0.45 | 0.1 | 0.32 | DGGDGGDHSSKLQrrrrrrrrVSrrFMrr | |
| G12 | 1.75 | 2.8 | 0.89 | 1.4 | 3.51 | 5.8 | RDVCRNFMRRYQSRVIQGLV (SEQ ID NO: 49) | |
| G12.1 | 7.65 | >10 | >10 | >10 | >10 | >10 | RDVSRNFMRRYQSRVIQGLV (SEQ ID NO: 50) | |
| G12.2 | 1.75 | 2.8 | 1.73 | 2.8 | 3.51 | 5.8 | RDVSRRFMRRYQSRVIQGLV (SEQ ID NO: 51) | |
| G12.3 | 3.51 | 5.7 | 3.5 | 5.5 | 7.7 | >10 | RDVSRRFMRRQSRVIQGLV (SEQ ID NO: 52) | |
| G12.15 | 0.89 | 1.4 | 0.42 | 0.69 | 1.75 | 2.8 | RDVARRFMRRQSRVISRLV (SEQ ID NO: 53) | |
| G12.22 | 0.87 | 1.38 | 0.89 | 1.39 | 3.5 | 5.7 | SDVARRFMRRQSRVIRRLV (SEQ ID NO: 54) | |
| G12.23 | 1 | 3 | >10 | >10 | 7.7 | >10 | SDVAKKFMKKQSKVIKKLV (SEQ ID NO: 55) | |
| G12.16 | 0.72 | 1.39 | 1 | 2.8 | 3.51 | 5.6 | RDvARrFMrrQSrVISrLV | |
| G12.17 | 0.89 | 3.3 | 1.6 | 2.8 | 1.75 | 2.8 | RDVaRrFMrrQSrVISRlV | |
| G12.18 | 1 | 2.9 | 1.61 | 2.8 | 3.51 | 5.6 | RDVaRRFMrrQsRViSRLV | |
| G12.4 | 2.85 | 5.7 | 3.51 | 5.5 | 3.5 | 5.5 | RDVARRFMRRYQARVIQGLV (SEQ ID NO: 56) | |
| G12.5 | 3.3 | 5.7 | >10 | >10 | 7.7 | >10 | RDVSRRFMrrYQSRVIQGLV (SEQ ID NO: 51) | |
| G12.6 | 0.89 | 1.45 | 0.9 | 1.45 | 0.42 | 0.7 | RRVSRRFMRRYQSRVIQGLV (SEQ ID NO: 57) | |
| G12.7 | 0.25 | 0.71 | 0.22 | 0.35 | 0.21 | 0.35 | RRVSRRFMRRYRSRVIRGLV (SEQ ID NO: 58) | YES |

TABLE 2-continued

| Peptide Name | E. coli DH5a IC50 (μM) | E. coli DH5a MIC (μM) | Salmonella IC50 (μM) | Salmonella MIC (μM) | B. cereus IC50 (μM) | B. cereus MIC (μM) | Sequence | Active in DMEM |
|---|---|---|---|---|---|---|---|---|
| G12.8 | 0.45 | 0.7 | 0.41 | 0.65 | 0.45 | 0.71 | RRVSRRFMRRYRSRRIRRLV (SEQ ID NO: 59) | YES |
| G12.34 | 0.11 | 0.2 | 0.21 | 0.78 | 0.12 | 0.31 | rrvsrrfmrryrsrrirrlv | YES |
| G12.9 | 0.49 | 1.35 | 0.85 | 1.4 | 3.51 | 5.6 | KKVSKKFMKKYQSKVIQGLV (SEQ ID NO: 60) | |
| G12.10 | 0.45 | 0.7 | 0.85 | 1.4 | 0.89 | 1.4 | RRVSRRFMRRYQSRVPQGLV (SEQ ID NO: 61) | |
| G12.24 | 0.42 | 0.8 | 0.7 | 1.4 | 0.42 | 0.8 | QRRSSRFMRRYQRVVPRGLV (SEQ ID NO: 62) | |
| G12.11 | 0.21 | 0.75 | 0.41 | 0.65 | 0.21 | 0.35 | RRVSRRFMRRYRSRRPRRLV (SEQ ID NO: 63) | YES |
| G12.35 | <.078 | 0.11 | 0.21 | 0.32 | 0.45 | 0.75 | rrvsrrfmrryrsrrprrlv | YES |
| G12.12 | 0.21 | 0.35 | 0.21 | 0.35 | 0.21 | 0.35 | RRVSRRPMRRYRSRRPRRLV (SEQ ID NO: 64) | YES |
| G12.19 | 0.22 | 0.75 | 0.73 | 1.38 | 0.21 | 0.35 | RRVSRPPPRRYRSRRPRRLV (SEQ ID NO: 65) | YES |
| G12.25 | <.078 | 0.15 | 0.1 | 1.25 | <.078 | <.078 | rrvsrpppmrryrsrrprrlv | YES |
| G12.20 | 0.23 | 0.73 | 0.42 | 1.4 | 0.21 | 0.35 | RRVSRPPMRRYRSRRPRRLV (SEQ ID NO: 66) | YES |
| G12.26 | <.078 | <.078 | 0.1 | 0.3 | <.078 | 0.35 | rrvsrppmrryrsrrprrlv | YES |
| G12.21 | <.078 | 0.2 | 0.21 | 0.35 | 0.21 | 0.35 | rrvsrpmrryrsrrprrlv (SEQ ID NO: 64) | YES |
| G12.27 CYC | <.078 | 0.1 | 0.21 | 0.37 | 0.45 | 0.7 | rrvsrpmrryrsrrprrlvD | YES |
| G12.28 | <.078 | 0.1 | 0.38 | 0.7 | 0.21 | 0.35 | kkvskkpmkkykskkpkklv | |
| G12.29 | 0.1 | 0.15 | 0.28 | 1.15 | 0.21 | 0.35 | kkkkkkvskkpmkkykskkpkklv | |
| G13 | 1.71 | 2.8 | >10 | >10 | 1.75 | 2.85 | QRSVSNAATRVCRTGRSRW (SEQ ID NO: 67) | |
| G13.1 | 7.45 | >10 | >10 | >10 | >10 | >10 | QRSVSNAATRVSRTGRSRW (SEQ ID NO: 68) | |
| G13.2 | 0.85 | 1.37 | 7.3 | >10 | 3.4 | 5.6 | QRSVSRAATRVSRTGRSRW (SEQ ID NO: 69) | |
| G13.13 | 0.38 | 5.1 | 1.4 | >10 | >10 | >10 | QRSVSRPPTRVSRPPRSRW (SEQ ID NO: 70) | |
| G13.6 | 1.65 | 2.8 | 7.48 | >10 | 7.7 | >10 | QRAVARAATRVARTGRARW (SEQ ID NO: 71) | |
| G13.7 | 2.85 | 5.7 | >10 | >10 | 7.7 | >10 | QRSVSRaaTRVSRTGRSRW | |
| G13.8 | 3.3 | 5.7 | >10 | >10 | 7.7 | >10 | QRSVSRAPTRVSRTGRSRW (SEQ ID NO: 72) | |
| G13.9 | 0.89 | 1.45 | >10 | >10 | 7.7 | >10 | QKSVSKAATKVSKTGKSKW (SEQ ID NO: 73) | |
| G13.11 | 2.72 | 5.75 | >10 | >10 | >10 | >10 | QRSVSRPPTRVSRTGRSRW (SEQ ID NO: 74) | |
| G13.12 | 1.75 | 5.65 | >10 | >10 | >10 | >10 | QRSVSRPPTRVSRTGRARW (SEQ ID NO: 75) | |
| G13.10 | 0.25 | 0.71 | >10 | >10 | 3.5 | 5.6 | QRSVSRAATRVCRTGRSNW (SEQ ID NO: 76) | |
| G14 | 0.89 | 1.37 | 0.89 | 1.37 | 1.75 | 2.8 | GRSRWRDVCRNFMRR (SEQ ID NO: 77) | |
| G14.1 | 0.89 | 1.37 | 1.75 | 2.8 | 7.66 | >10 | GRSRWRDVSRNFMRR (SEQ ID NO: 78) | |
| G14.12 | 6.75 | >10 | >10 | >10 | >10 | >10 | GRSGWRDVSRNFRRG (SEQ ID NO: 79) | |
| G14.13 | 1.85 | 5.6 | 7.6 | >10 | >10 | >10 | GRSLWRDVSRNFMRR (SEQ ID NO: 80) | |
| G14.2 | 0.85 | 1.45 | 0.86 | 1.4 | 1.75 | 2.8 | GRSRWRDVSRRFMRR (SEQ ID NO: 81) | |
| G14.9 | 0.81 | 1.38 | 0.44 | 0.65 | 0.85 | 1.37 | GRARWRDVARRFMRR (SEQ ID NO: 82) | |
| G14.10 | 0.45 | 1.25 | 0.89 | 1.4 | 1.75 | 2.8 | GRSRWrdVSRRFMRR (SEQ ID NO: 81) | |
| G14.11 | 0.45 | 0.7 | 0.44 | 0.65 | 0.45 | 0.7 | GRSRWRRVSRRFMRR (SEQ ID NO: 83) | YES |
| G14.15 | <.078 | 0.1 | 0.15 | 0.35 | <.078 | 0.2 | grsrwrrvsrrfmrr (SEQ ID NO: 83) | YES |
| G14.14 | 0.11 | 0.17 | 0.21 | 0.7 | 0.21 | 0.35 | GSRRWRDVSRRFMRR (SEQ ID NO: 84) | |
| G20.1 | 0.43 | 0.7 | 0.42 | 0.7 | 0.45 | 0.71 | GRSRWRDVSRNFMRRYQSRVIQGLV (SEQ ID NO: 85) | |
| G21 | 0.23 | 0.35 | 0.21 | 0.35 | 0.2 | 1 | QRSVSNAATRVSRTGRSRWRDVSRNFMRRYQSRVIQGLV (SEQ ID NO: 86) | |

Table 2 give the peptide sequences and data; peptides are designated according to a "parent sequence" having a native granulysin subsequence, and derivatives, e.g., 8.1 derived from 8. For Table 2, the original "wild type" granulysin sequence is at the top of each group of peptides, namely groups G8, G11, G12, and G14, named as in the previous publication by Wang et al. The first column is the peptide name, which is based on the nearest "native" peptide. Thus, G8 is based on granulysin helices 2/loop 2/3. G8.1 contains two cysteine→serine substitutions in G8. (G8.1 is the same as G9).

In Table 2, Columns 2-7 are the MIC and IC50 (concentration required for 50% inhibition of growth) for each organism (*E. coli, Salmonella*, and *B. cereus*). The MIC (minimum inhibitory concentration) was determined as described above, in a multiwell plate assay. Column 8 shows the sequence for each peptide using standard one letter code for each amino acid. L-isomer amino acids are designated by capital letters while D-isomer amino acids are designated by lower case letters.

Many cationic antimicrobial peptides are inactive under "physiologic" conditions, e.g., in the presence of salts, ions, and/or serum. The peptides listed in Table 2 were tested in DMEM and RPMI, media that approximate blood and tissue conditions in vivo and those that were active under these conditions are listed in the last column (active in DMEM). In addition, peptides that contain some or all D-isomer amino acids are more active in DMEM. No peptides that were all L-isomer peptides lysed bacteria in DMEM supplemented with serum.

TABLE 3

| Peptide Name | Hydrophobic residues | glycine + proline residues | Neg chgd residue | Pos chgd res. | Net pos chg | Hydrophobic moment | Active DMEM | Lyse U937 | Lyse PBMC |
|---|---|---|---|---|---|---|---|---|---|
| G8 | 10 | 1 | 1 | 9 | 8 | 13.65 | | Y | |
| G8.1 | 8 | 1 | 1 | 9 | 8 | 12.98 | | | |
| G8.16 | 5 | 6 | 1 | 9 | 8 | 12.17 | | | |
| G8.17 | | | | | | 12.98 | | | |
| G8.2 | 8 | 1 | 1 | 10 | 9 | 13.86 | | | |
| G8.3 | 8 | 1 | 1 | 10 | 9 | 13.25 | | | |
| G8.15 | 8 | 2 | 1 | 10 | 9 | 13.83 | | | |
| G8.4 | 8 | 1 | 1 | 11 | 10 | 14.1 | | | |
| G8.5 | 13 | 1 | 1 | 10 | 9 | 13.86 | | | |
| G8.6 | 13 | 1 | 1 | 10 | 9 | 13.24 | Y | Y | |
| G8.7 | 13 | 1 | 1 | 11 | 10 | 14.09 | | Y | |
| G8.8 | 8 | 1 | 1 | 11 | 10 | | Y | | |
| G8.11 | 6 | 3 | 1 | 11 | 10 | | Y | | |
| G8.12 | 6 | 3 | 1 | 11 | 10 | 14.36 | Y | | |
| G8.9 | 8 | 1 | 0 | 12 | 12 | 12.62 | Y | | |
| G8.10 | 13 | 1 | 0 | 12 | 12 | 12.61 | Y | Y | |
| G11 | 4 | 0 | 1 | 4 | 3 | 9.02 | | | |
| G11.36 | 8 | 2 | 2 | 10 | 8 | 2.5 | | Y | |
| G11.6 | 6 | 1 | 2 | 10 | 8 | 8.13 | | | |
| G11.26 | 9 | 2 | 3 | 15 | 12 | 1.16 | Y | | |
| G11.7 | 6 | 1 | 0 | 12 | 12 | 6.34 | Y | Y | |
| G11.10 | 9 | 2 | 0 | 18 | 18 | 1.16 | Y | Y | |
| G11.24 | 3 | 0 | 0 | 6 | 6 | | | | |
| G11.29cyc | 5 | 0 | 0 | 6 | 6 | | Y | | |
| G11.30cyc | 3 | 0 | 0 | 6 | 6 | | | | |
| G11.31cyc | 8 | 1 | 0 | 12 | 12 | | | | |
| G11.32cyc | 3 | 0 | 0 | 6 | 6 | | Y | | |
| G11.34 | 3 | 0 | 0 | 6 | 6 | | Y | | |
| G11.35 | 3 | 0 | 0 | 6 | 6 | | Y | | |
| G11.27 | | | | | | | Y | Y | Y |
| G11.16 | 4 | 0 | 0 | 6 | 6 | 8.17 | | | |
| G11.19 | 4 | 0 | 0 | 6 | 6 | 7.97 | | | |
| G11.20 | 4 | 0 | 0 | 6 | 6 | 8.91 | | | |
| G11.23 | 8 | 1 | 0 | 12 | 12 | 7.89 | Y | Y | |
| G11.8 | 3 | 0 | 0 | 6 | 6 | 10.62 | | | |
| G11.15 | 6 | 1 | 0 | 14 | 14 | 9.56 | | | |
| G11.25 | 9 | 2 | 0 | 18 | 18 | 1.16 | Y | Y | |
| G11.46 | 3 | 0 | 0 | 11 | 11 | 3.82 | Y | | |
| G12 | 8 | 1 | 1 | 5 | 4 | 7.75 | | | |
| G12.1 | 7 | 1 | 1 | 5 | 4 | 7.27 | | | |
| G12.2 | 7 | 1 | 1 | 6 | 5 | 8.13 | | | |
| G12.3 | 7 | 1 | 1 | 6 | 5 | 13.49 | | | |
| G12.15 | 8 | 0 | 1 | 7 | 6 | 13.5 | | | |
| G12.16 | 8 | 0 | 1 | 7 | 6 | | | | |
| G12.17 | 8 | 0 | 1 | 7 | 6 | | | | |
| G12.18 | 8 | 0 | 1 | 7 | 6 | | | | |
| G12.4 | 9 | 1 | 1 | 6 | 5 | 8.13 | | | |
| G12.5 | 7 | 1 | 1 | 6 | 5 | | | | |
| G12.6 | 7 | 1 | 0 | 7 | 7 | 6.38 | | | |
| G12.7 | 7 | 1 | 0 | 9 | 9 | 7.01 | Y | Y | |
| G12.8 | 6 | 0 | 0 | 11 | 11 | 4.43 | Y | Y | |
| G12.34 | | | | | | | Y | Y | Y |
| G12.9 | 7 | 1 | 0 | 7 | 7 | 9.03 | | | |
| G12.10 | 6 | 2 | 0 | 7 | 7 | 7.11 | | Y | |
| G12.11 | 5 | 1 | 0 | 11 | 11 | 5.33 | Y | | |

TABLE 3-continued

| Peptide Name | Hydrophobic residues | glycine + proline residues | Neg chgd residue | Pos chgd res. | Net pos chg | Hydrophobic moment | Active DMEM | Lyse U937 | Lyse PBMC |
|---|---|---|---|---|---|---|---|---|---|
| G12.35 | | | | | | | Y | Y | Y |
| G12.12 | 4 | 2 | 0 | 11 | 11 | 4.07 | Y | | |
| G12.21 | 4 | 2 | 0 | 11 | 11 | | Y | | |
| G12.27 | | | | | | | Y | | |
| G12.19 | 3 | 4 | 0 | 10 | 10 | 2.31 | Y | | |
| G12.25 | 3 | 4 | 0 | 10 | 10 | | Y | | |
| G12.20 | 4 | 3 | 0 | 10 | 10 | 2.63 | Y | | |
| G12.26 | 4 | 3 | 0 | 10 | 10 | | Y | | |
| G13 | 6 | 1 | 0 | 5 | 5 | 5.58 | | | |
| G13.1 | 5 | 1 | 0 | 5 | 5 | 5.36 | | | |
| G13.2 | 5 | 1 | 0 | 6 | 6 | 6.31 | | | |
| G13.4 | 5 | 1 | 0 | 5 | 5 | 6.94 | | | |
| G13.5 | 5 | 1 | 0 | 4 | 4 | 6.65 | | | |
| G13.6 | 9 | 1 | 0 | 6 | 6 | 6.35 | | | |
| G13.7 | 5 | 1 | 0 | 6 | 6 | | | | |
| G13.8 | 4 | 2 | 0 | 6 | 6 | 6.65 | | | |
| G13.9 | 5 | 1 | 0 | 6 | 6 | 9.45 | | | |
| G13.10 | 6 | 1 | 0 | 5 | 5 | 7.07 | | | |
| G14 | 5 | 1 | 1 | 6 | 5 | 10.15 | | Y | |
| G14.1 | 4 | 1 | 1 | 6 | 5 | 9.74 | | | |
| G14.12 | 3 | 3 | 1 | 5 | 4 | 9.66 | | | |
| G14.13 | 5 | 1 | 1 | 5 | 4 | 9.38 | | | |
| G14.2 | 4 | 1 | 1 | 7 | 6 | 10.34 | | | |
| G14.9 | 6 | 1 | 1 | 7 | 6 | 10.34 | | | |
| G14.10 | 4 | 1 | 1 | 7 | 6 | | | | |
| G14.11 | 4 | 1 | 0 | 8 | 8 | 8.54 | Y | | |
| G14.15 | 4 | 1 | 0 | 8 | 8 | | Y | | Y |

Table 3 lists the physical properties of the exemplified peptides. Column 2 shows the number of hydrophobic residues; column 3 shows the number of glycine and prolines in each peptide; column 4 shows the number of negatively charged residues; column 5 shows the number of positively charged residues; column 6 shows the net positive charge. The hydrophobic moment is a measure of amphipathicity and indicates how well the hydrophobic residues fall on one side of the helix while the hydrophilic residues fall on the opposite side is shown in column 7. This was determined using the Membrane Explorer Program (http://blanco.biomol.uci.edu/mpex/). A high number indicates a high hydrophobic moment. Column 8 again (like Table 2) indicates which of these peptides is active in DMEM.

Columns 9 and 10 refer to the effects of these peptides on human cells. The effects were tested in two ways. First, peptides were tested for the ability to lyse tumor cells, as judged by induction of apoptosis in the monocyte-like cell line U937. U937 cells were cultured overnight in DMEM supplemented with 10% FCS plus 1 μCi/ml $^3$H-thymidine. The next day, cells were washed and cultured in DMEM/10% FCS in the presence of 50 μM peptide for 4-6 hours. Cells were then harvested and $^3$H-thymidine determined by beta-scintillation counting. Apoptosis results in DNA fragmentation, so the $^3$H-thymidine is reduced in cells undergoing apoptosis. Only 3 peptides, G8, G12.34, and G12.35 cause apoptosis of tumor cells.

The second assay for effects on mammalian cells involved isolating human peripheral blood mononuclear cells (PBMC) and testing peptide induced uptake of propidium iodide (PI), a measure of membrane disruption. PBMC were cultured in DMEM/10% FCS in the presence of 50 μM peptide for three hours and PI uptake was determined using a fluorescence activated cell analyzer. Peptides G12.34, G12.35 and G14.15 were the only peptides that caused PI uptake in normal human PBMC. Thus, the vast majority of granulysin peptide derivatives are not toxic to mammalian cells even at high concentrations.

Peptide Synthesis

The present peptides were prepared by standard F-moc chemistry as described in Wang et al. The cyclic peptides 11.30, 11.30, 11.31, 11.32, and 12.27 were cyclized as follows:

Cyclic Peptide Synthesis

The peptides were synthesized by the by the standard SPPS protocol [1], applying—fluorenylmetoxycarbonyl (Fmoc-) chemistry [Chang, C.; Meienhofer, *J Int. J. Pept. Res.*, 1978, 11, 246-249, Carpino, L. A.; Han, G. Y. *J. Org. Chem.* 1972, 37, 3404-3409] and (HBTU/HOBT/NMM) coupling in N-methylpyrrolidone (NMP, single coupling, 1×50 min) with a five-fold excess of reagents. N$^α$-Fmoc deprotection was achieved with 20% piperidine/NMP (3×5 min). Side-chain protection was afforded by following: tert-butyl esters for Ser, Boc for Lys, Trt for Cys, ODmab for Asp and Pbf for Arg.

Peptide Bond Formation for Cyclic Peptides

Starting from Fmoc-Asp(Rink-amide-MBHA resin)-ODmab we synthesized the linear peptides Fmoc-RRSVR-RFMRRD(resin)-ODmab (SEQ ID NO: 87), Fmoc-KKVSKKFMKKGSKKVSKKFMKKD(resin)-ODmab (SEQ ID NO: 88). After deprotection of the C-terminal carboxyl function of Asp (anchored to the resin via its side chain) by flowing 2% hydrazine monohydrate in DMF through the resin bed (2×10 min), the Fmoc-group was removed. On-resin cyclization was achieved by (1 equiv) coupling reagent HCTU in the presence of DIPEA (2 equiv.) for 18 h. The cleavages from the resins were carried out in 6 h, at room temperature, with TFA/TIS/water/EDT (90%:1%:5%:4%). The crude products were precipitated with diethyl ether, centrifuged, re-dissolved in H$_2$O and lyophilized. Peptides were purified by RP-HPLC to 95% homogeneity.

Disulfide Bond Formation for Cyclic Peptides

The synthesis was performed using standard Fmoc methodology. The peptides were assembled on Rink-amide-MBHA resin. The following linear peptides Cys(Trt)-RRS-VRRFMRR-Cys(Trt)-resin (SEQ ID NO: 89), Cys(Trt)-KKVSKKFMKKGSKKVSKKFMKK-Cys(Trt)-resin (SEQ ID NO: 90), were synthesized. Disulfide cyclization was performed on the solid phase by thallium trifluoroacetate in DMF for 18 h. Deprotection of the remaining amino acid side chains and cleavage of the amide-peptide from the resin was performed by incubation the peptide-resin with TFA/water/TIS (94.5%:2.5%:3.5%) for 6 h at room temperature. The crude peptides were precipitated with diethyl ether, centrifuged, re-dissolved in H2O and lyophilized. Peptides were purified by RP-HPLC to 95% homogeneity.

Sequence Variation

Based on the work described herein, one could introduce certain modifications to the sequences disclosed. These sequences are guided by the following principles:
1. replacement of cysteine with serine abrogates lysis of human tumor cells
2. increasing the net positive charge is beneficial (to a point) only those peptides with a net positive charge of 8 or more are bactericidal in DMEM
3. substitution with some or all D- instead of L-amino acids enhances activity
4. inclusion of proline to disrupt the alpha helix is beneficial
5. cyclization (G11.30 and G11.32) is beneficial
6. dimers or trimers show enhanced activity
7. decreasing the number of hydrophobic residues is beneficial
8. decreasing the hydrophobic moment is beneficial
9. substitution of arginine with lysine decreases or abrogates antimicrobial activity Inclusion of charged residues such as lysine, arginine and histidine is desirable in the present peptides. For example, preferred G12.21 contains 11/20 arginine resides; G11.46 contains 11/15 arginine residues; and G11.15 contains 8/15 arginine residues.

In addition, one may refer to the native granulysin subsequences indicated in connection with SEQ ID NOs: 1 and 2. Given the data and principles presented here, one may expect to be able to change 20% to 50% of a given sequence according to the above guidelines. In general, the peptides of the present invention will have (50% to 80%, preferably at least 70%) sequence identity to the sequences literally disclosed herein, depending on the reference sequence considered. That is, for example, in a 21 residue peptide, at least 14 residues will be identical to the disclosed sequence, or, for 80% identity 16 residues, with the remaining being those selected according to the design choices given herein (e.g., addition of prolines, replacement of cysteine(s); inclusion of positively charged amino acids such as K and R). A gap would count as a single mismatch. The identity referred to here is local sequence identity, that is, for example, if the reference sequence is 30 amino acids long and the test sequence is 14 amino acids long, only the 14 amino acids are considered, and gaps are allowed, as stated. Substitution of D for L amino acids is also contemplated herein, but would not change the sequence identity. In addition, the sequences (which range from 10 to 29 amino acids in length) could be lengthened according to the known sequence of granulysin; or could be lengthened by "dimerization," or oligomerization, that is, repeating all or a portion of a helical sequence contained in a sequence given herein. They may also be cyclized, as exemplified by G11.30 and 11.32. They may be synthesized as "dendrimers", i.e., multiple peptides attached to a core. A method for synthesis of peptide dendrimers is provided, e.g., in "NCAM binding compounds," U.S. Pat. No. 6,887,844, hereby incorporated by reference. The present peptides may contain other modifications, such as fatty acid extensions or other organic molecules. None of these modifications affect the sequence identity as defined here.

The amino acids used in peptides according to the present invention could be modified in a number of ways. They may be D- or L-amino acids, or may be non-naturally occurring amino acids as discussed above. They may also be joined by modifications of the standard peptide bond, e.g., as peptoids. Both β-peptides and peptoids may be used to impart protease resistance, again without affecting sequence identity. An example of a 50% identical sequence is given below:

| | | | | | | | | | | | | | | | | | | | |
|---|---|---|---|---|---|---|---|---|---|---|---|---|---|---|---|---|---|---|---|
| G12 (SEQ ID NO: 49) | R | D | V | C | R | N | F | M | R | R | Y | Q | S | R | V | I | Q | G | L | V |
| G12.21 | r | r | v | s | r | r | p | m | r | r | y | r | s | r | r | p | r | r | l | v |
| identical? | y | n | y | n | y | n | n | y | y | y | y | n | y | y | n | n | n | n | n | y |

In addition, the present peptides may be prepared as other modifications including recombinant linear oligomers (2, 4, 6, and 8 units/molecule) expressed in *E. coli*, dendrimers (multiple peptides emanating from a central core), and peptide/antibody complexes to target peptides to specific targets.

A representation of desirable properties is given below in Table 4.

TABLE 4

| Peptide | Sequence | MIC (μM) | % α-helix | Hydrophobic residues | Net positive charge | Hydrophobic moment |
|---|---|---|---|---|---|---|
| G8.17 | qrsvsnaatrvsrtgrsrwrdvsrnfmrr | 0.75 | 40 | 8 | 8 | 12.98 |
| G12.21 | rrvsrrpmrryrsrrprrlv | 0.2 | 0 | 4 | 11 | 4.07 |
| G11.46 | rrrrrrVSrrFMrr | 0.8 | 0 | 3 | 11 | 5.44 |
| G14.15 | grsrwrrvsrrfmrr | 0.3 | 33 | 4 | 8 | 8.54 |

Table 4 further illustrates properties of desirable peptides. The MIC values are for *E. coli* in 10 mM phosphate buffer. The peptides were derived by the inventors from granulysin helix 3. Peptide G8.17 loses all activity in DMEM, and thus is not an ideal candidate. It contains an equal number of hydrophobic and positively charged amino acids, can adapt an αhelical structure, and is very amphipathic. In contrast, the remaining 3 peptides all retain activity in DMEM even in the presence of serum. These peptides contain more positive residues than hydrophobic residues. G12.21 contains 2 proline residues, G11.46 is based on a modification of the helix three sequence (RRVSRRFMRR) (SEQ ID NO: 91) with a 5 arginine extension at the NH2 terminus, and G14.15 includes loop 2/RRVSRRFMRR (SEQ ID NO: 91). G12.21 and G11.46 are random coils in aqueous solution or in TFE (2,2, 2-trifluoroethanol) that mimics biologic membranes. G14.15 contains some alpha helical content, and is thus intermediate between random coil peptides and highly helical peptides like G8 or G8.1. Interestingly, substitution of all arginines with lysine in G12.21 (new peptide designated G12.28) results in an inactive peptide, emphasizing the importance of arginine.

The above peptides G12.21, 11.46, and 14.15 lyse both gram negative bacteria and gram negative bacteria, as well as fungi when tested in either 10 mM phosphate buffer or DMEM.

The peptide series G12.34, G12.35, G12.21, G12.25, and G12.26 offer some insight into what makes a good antimicrobial agent. G12.34 is the "parent" sequence. It has some alpha helical content and is somewhat lytic against mammalian cells. G12.35 has a single substitution (proline for isoleucine at position 16). It contains less alpha helix and is somewhat less toxic against mammalian cells. G12.21 contains one more substitution (proline for phenylalanine at position 7) and is a random coil with no toxicity. G12.26 contains the substitution of proline for methionine at position 8 and loses some antibacterial activity compared to G12.21. G12.25 contains another proline at position 8 and has lost much of its antibacterial activity.

It is contemplated that specific modifications may be made within the peptide that maintain the peptides antimicrobial properties of the claimed sequence, but also confers some additional desirable property to the peptide. It is well known in the art that certain amino acids may be substituted for other amino acids in a protein structure without appreciable loss of peptide activity. Since it is the interactive capacity and nature of a peptide that defines that peptide's biological functional activity, certain amino acid sequence substitutions can be made in a protein sequence (or, of course, its underlying DNA coding sequence) and nevertheless obtain a peptide with like properties. It is thus contemplated by the inventors that various changes may be made in the sequence of the present peptides or the underlying nucleic acids, without appreciable loss of biological utility or activity and perhaps may enhance desired activities.

For example, in designing peptide constructs with antimicrobial properties, substitutions may be used which modulate one or more properties of the molecule. Such variants typically contain the exchange of one amino acid for another at one or more sites within the peptide. For example, certain amino acids may be substituted for other amino acids in a peptide structure in order to enhance the interactive binding capacity of the structures. Since it is the interactive capacity and nature of a protein that defines that protein's biological functional activity, certain amino acid substitutions can be made in a protein sequence, and its underlying DNA coding sequence, which potentially creates a peptide with superior characteristics.

In making such changes, the hydropathic index of amino acids may be considered.

The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±0.2 is preferred, those which are within ±0.1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±0.1); glutamate (+3.0±0.1); serine (+0.3); asparagine (+0.2); glutamine (+0.2); glycine (0); threonine (−0.4); proline (−0.5±0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Amino acid substitutions are generally based on the relative similarity of the amino acid side-chain substituents, for example, their hydrophobicity, hydrophilicity, charge, size, and the like but may nevertheless be made to highlight a particular property of the peptide. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

The present variant peptides are synthesized and tested as described above. They will have the following properties:

A MIC, preferably for three different organisms which totals 10 µM, preferably 5.0 µM or less. The MIC total is preferably calculated from three members of the group of: *B. cereus, Staph. A, E. coli, Salmonella typhimurium* or *S. aureus*. Although it is preferably 5.0 or less, it is more preferably less than 2, most preferably less than 1.5. It is preferably less than 1.0 μM for a single organism. It should be understood that the advantageous activities of the present peptides may in certain embodiments be measured other than by MIC, which is described below in buffer (for present purposes). Other measurements of activity are also described here, such as cfu formation and activity in DMEM. Furthermore, the antimicrobial peptide shows negligible lysis of mammalian cells, as exemplified by PI uptake less than 10% of medium control. The present peptides are expected to be active against a variety of other organisms, including *Listeria* spp., *S. aureus, C. albicans, Cryptococcus neoformans, Leishmania major*, etc. We have shown that some of them are active against *C. albicans, Listeria, S. aureus, C. neoformans, P. aeruginosa*. The MIC may be tested against other organisms than the exemplary *E. coli, Salmonella typhimurium* and *B. cereus* in order to identify potent antimicrobial peptides.

The present peptides have been shown to be active against both gram positive and gram negative bacteria. The peptides that show the highest activity are not amphipathic and do not adapt an alpha helical structure. Thus, organisms that share similar cell walls and membranes will have similar susceptibility to a given peptide.

The sequence may be extended beyond that shown above by reference to the granulysin helix 3 flanking regions. The peptide may preferably comprise up to about 40 amino acids (the longest peptide in the table is 34 amino acids e.g., G11.26), with the maximum length given by SEQ ID NO:2. As shown in SEQ ID NO: 2, the range of amino acid residues used in the present invention spans about 40 residues. A peptide according to the present invention also should preferably comprise at least from 5% to 100%, preferably more than 50% D-amino acids.

Administration

It is contemplated that the present peptides will be prepared in pharmaceutical form and will be sterilized and mixed with excipients suitable for injection. The formulations are subjected to preclinical testing as is known in the art. The present peptides may be tested for suitable toxicity, absorption, distribution, metabolism and excretion (ADME) for human and/or veterinary applications.

The composition of the present invention may be administered for clinical use, in a therapeutically effective amount and composition, to beings infected with a microorganism discussed above. Beings treatable clinically include all land, air and water animals, and plants, but preferably mammals and most preferably humans. Alternatively, the composition may be administered prophylactically. The therapeutic and prophylactic dose for the present invention may vary according to several factors including the age, weight, and condition of the individual, route of administration and/or other drug interactions. The principles and factors for determining dosage are not discussed here in detail, but are known in the art and may be referenced in pages 1-83 of GOODMAN AND GILMAN'S THE PHARMACOLOGICAL BASIS OF THERAPEUTICS (8th Edition). The preferred doses for therapeutic and prophylactic treatment may vary and can be adjusted to suit the individual and situation. The peptides of this invention may be delivered in a pharmaceutically acceptable composition suitable for any of the routes of administration discussed above.

"Pharmaceutically acceptable" is used herein to refer to those materials which are within the scope of sound medical judgment, suitable for use in contact with the tissue of humans and lower animals, avian and aquatic organisms without undue toxicity, irritation, allergic response and the like commensurate with a reasonable benefit/risk ratio, and effective for their intended use in the composition.

The pharmaceutical composition may include, but is not limited to, at least one acceptable carrier. The carrier is generally an inert bulk agent added to make the active ingredients easier to handle and can be solid, semisolid or liquid in the usual manner as well as understood in the art. Such a carrier may be a solvent, diluent or carrier comprising of waxes, cellulose derivatives, mineral oils, vegetable oils, petroleum derivatives, water, anhydrous lanolin, white petrolatum, liquid petrolatum, olive oil, ethanol and ethanol-polysorbate 80 solutions, propylene glycol-water solutions, and jojoba oils, methylcellulose or paraffin, beeswax, glyceryl stearate, PEG-2 stearate, propylene glycol stearate, glycol stearate, cetyl alcohol, stearyl alcohol, and any mixture thereof. Carriers used may include commercially available carriers or vehicles including Aquaphor ointment base (Beirsdorf Inc.,), Eucerin® creme/lotion (Beirsdorf), Acid Mantle® (Sandoz), Nutraderm® creme/lotion (Owen), Vehicle/N® or Vehicle/N® Mild (Neutrogena).

Pharmaceutical compositions of the invention may also include any delivery vehicle or device known in the art to enhance the transport of peptides across tissue and/or cell surfaces to reach the circulatory system and/or target site. Such delivery vehicles or devices may include liposomes or immunogenic liposomes, which may be administered in admixture with any carrier (discussed above) with regard to the intended route of administration, and standard pharmaceutical practice. Dosages of peptides associated with such delivery vehicles or devices will vary according to certain factors including the age, weight, and condition of the individual, as well as the pharmacokinetics and release characteristics of the peptide from the delivery vehicles or devices. Further, the ratio of peptide to liposome and carrier will depend on the chemical nature, solubility, trapping efficiency, and stability of the peptide, as well as the dosage anticipated. Maximal delivery of the peptide of the present invention may be accomplished by varying the lipid:peptide ratio as well as the type of peptide and liposome used.

The pharmaceutical compositions of the invention may furthermore comprise salts for adjusting the tonicity and/or an excipient in order to facilitate the processing thereof, e.g., lyophilization and the rapid and complete dissolution of a lyophilized formulation when reconstituting the formulation before use. The term "salts" is used to designate additional agents for facilitating the processing or reconstitution of pharmaceutical preparations comprises conventional additives such as alkaline metal, alkaline earth metal or ammonium salts of organic acids such as citric acid, tartaric acid or acetic acid, e.g., sodium citrate, sodium tartrate or sodium acetate, or of mineral acids such as hydrochloric acid, e.g., sodium chloride. An excipient may be selected from disaccharides such as lactose, trehalose, and sucrose, sugar alcohols such as sorbitol or mannitol, polysaccharides such as the polymers commercialized as Dextran products such as Dextran® 40, Dextran® or Dextran 75, and Ficoll® and polyvalent alcohols such as polyethylene glycol or polyvinyl alcohol or a combination of two or more of these.

In addition, the compositions of the present invention may be used to form contact-killing coatings or layers on a variety of substrates including personal care products (such as toothbrushes, contact lens cases and dental equipment), healthcare products, household products, food preparation surfaces and packaging, and laboratory and scientific equipment. Further, other substrates include medical devices such as catheters, urological devices, blood collection and transfer devices, tracheotomy devices, intraocular lenses, wound dressings, sutures, surgical staples, membranes, shunts, gloves, tissue patches, prosthetic devices (e.g., heart valves) and wound drainage tubes. Still further, other substrates include textile products such as carpets and fabrics, paints and joint cement. A further use is as an antimicrobial soil fumigant.

In addition, the peptides of the present invention may be formulated for other routes of delivery besides injection (iv, im, sc) including nasal, oral, topical, etc. In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

An oral formulation may be prepared by known processes, e.g., U.S. Pat. No. 6,521,253.

A filler with disintegrant properties is selected from the group consisting of cellulose per (such as microcrystalline cellulose, microfine cellulose) starch per se (such as maize starch, sodium starch glycollate, potato starch, rice starch, wheat starch). A nonswelling filler is selected from the group sugars (such as mannitol, sorbitol, dextrose, xylitol, sucrose, laktos).

A disintegrant is selected from the group consisting of cellulose per se (such as microcrystalline cellulose, microfine cellulose, cross-linked sodium carboxymethyl cellulose, cross-linked hydroxypropyl cellulose), starch per se (such as sodium starch glycollate, pregelatinised starch, maize starch, potato starch, rice starch, wheat starch) and others (such as cross linked polyvinylpyrrolidone, cationic exchange resin). A binder is selected from the group consisting of cellulose per se (such as sodium carboxymethylcellulose, hydroxypropyl cellulose, hydroxypropyl methylcellulose, methyl cellulose), polymers (such as polyvinylpyrrolidone, polyethylene glycol), gelatins (such as hydrolysed gelatin), and traditional binders (such as starch, natural gums). Finally, a lubricant may be selected from the group consisting of insoluble lubricants (such as magnesium stearate, calcium stearate, zinc stearate, stearic acid, oils, talc, sodium stearyl fumarate), and soluble lubricants (such as polyethylene glycol, sodium benzoate, sodium lauryl sulfate).

Antimicrobial Activity

In the context of bacterial or microbial infections, a wide variety of potential pathogens may be found to be susceptible to the present peptides. As an exemplary list, bacterial infections, are deemed to include, but not be limited to, the 83 or more distinct serotypes of pneumococci, streptococci such as S. pyrogenes, S. agalactiae, S. equi, S. canis, S. bovis, S. equinus, S. anginosus, S. sanguis, S. salivarius, S. mitis, S. mutans, other viridans streptococci, peptostreptococci, other related species of streptococci, enterococci such as Enterococcus faecalis, Enterococcus faecium, Staphylococci, such as Staphylococcus epidermidis, Staphylococcus aureus, particularly in the nasopharynx, Hemophilus influenzae, pseudomonas species such as Pseudomonas aeruginosa, Pseudomonas pseudomallei, Pseudomonas mallei, brucellas such as Brucella melitensis, Brucella suis, Brucella abortus, Bordetella pertussis, Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi, Listeria monocytogenes, Nocardia asteroides, Bacteroides species, Actinomycetes species, Treponema pallidum, Leptospirosa species and related organisms. The invention may also be useful against gram negative bacteria such as Klebsiella pneumoniae, Escherichia coli, Proteus, Serratia species, Acinetobacter, Yersinia pestis, Francisella tularensis, Enterobacter species, Bacteriodes and Legionella species and the like. In addition, the invention may prove useful in controlling protozoan or macroscopic infections by organisms such as Cryptosporidium, Isospora belli, Toxoplasma gondii, Trichomonas vaginalis, Cyclospora species, for example, and for Chlamydia trachomatis and other Chlamydia infections such as Chlamydia psittaci, or Chlamydia pneumoniae, for example.

Figure 4:
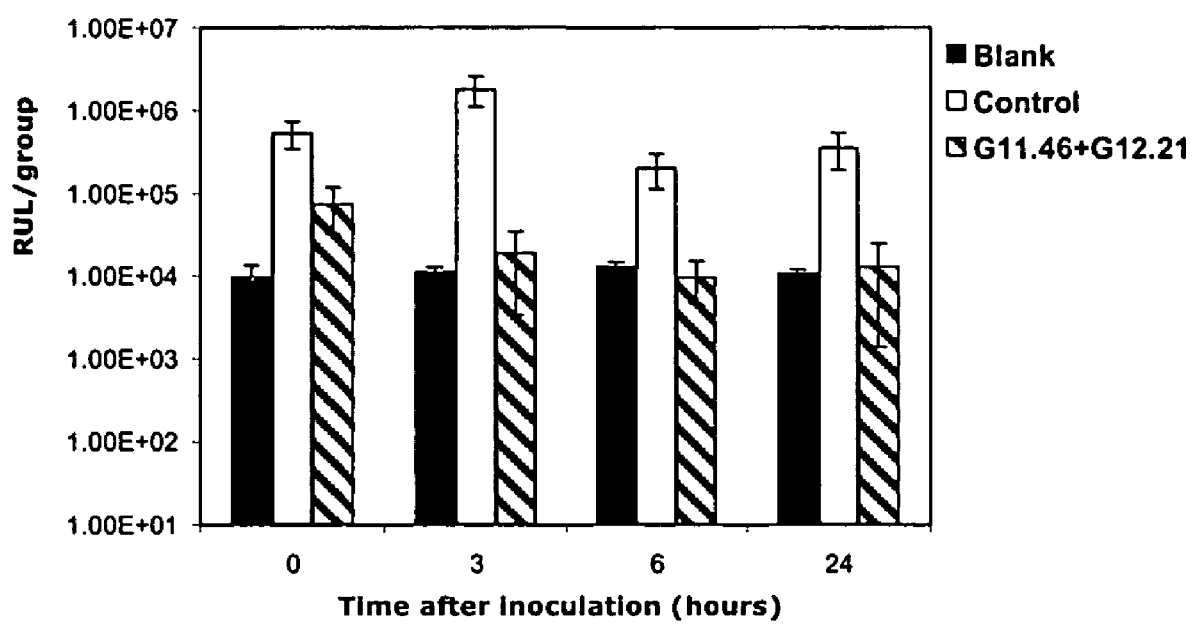
FIG. 4 is a bar graph showing the effects of G11.46 combined with G12.21 on *S. aureus* infection in vivo.
Figure 5:
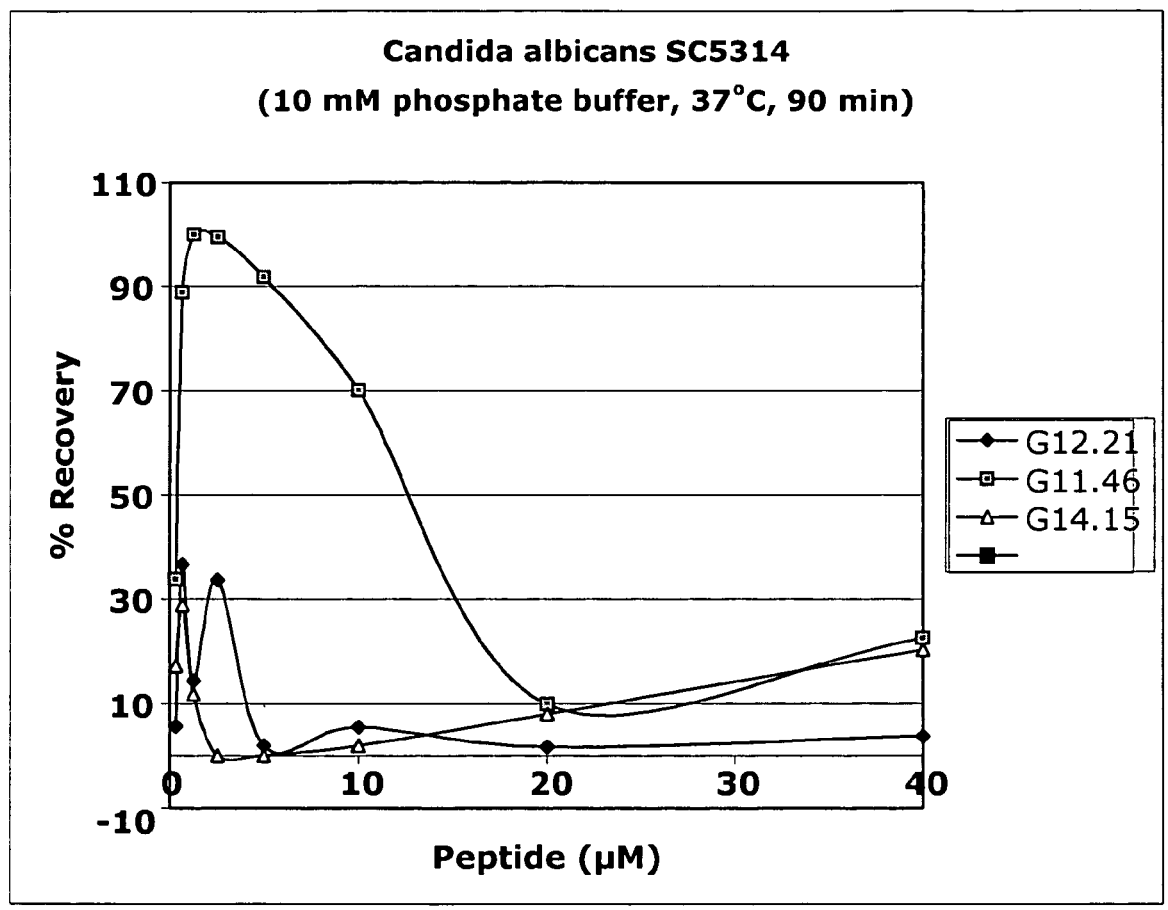
FIG. 5 is a graph showing the percent survival of *Candida albicans* by peptides G12.21, G11.46 and G14.5 at different concentrations.

The microorganism, e.g., bacterium, or population thereof, may be contacted either in vitro or in vivo. Contacting in vivo may be achieved by administering to an animal (including a human patient) that has, or is suspected to have a microbial or bacterial infection, a therapeutically effective amount of pharmacologically acceptable antimicrobial peptide formulation in alone or in combination with a therapeutic amount of a pharmacologically acceptable formulation of a antibiotic agent. The invention may thus be employed to treat both systemic and localized microbial and bacterial infections by introducing the combination of agents into the general circulation or by applying the combination, e.g., topically to a specific site, such as a wound or burn, or to the eye, ear or other site of infection.

Where an antimicrobial peptide is used in combination with other antimicrobial agents or antibiotics, an "effective amount of an antimicrobial agent or antibiotic" means an amount, or dose, within the range normally given or prescribed. Such ranges are well established in routine clinical practice and will thus be known to those of skill in the art. Appropriate oral and parenteral doses and treatment regimens may be obtained from dosages given in Tables 6-9 and FIGS. 1-5. FIG. 5 relates to Candida albicans, and the present peptides are expected to show activity against other yeast and fungi. As this invention provides for enhanced microbial and/or bacterial killing, it will be appreciated that effective amounts of an antimicrobial agent or antibiotic may be used that are lower than the standard doses previously recommended when the antimicrobial or antibiotic is combined with a antimicrobial peptide.

Dosages and Formulations

Naturally, in confirming the optimal therapeutic dose for antimicrobial peptides, first animal studies and then clinical trials would be conducted, as is routinely practiced in the art. Animal studies are common in the art and are further described in publications such as Lorian (1991, pp. 746-786, incorporated herein by reference) and Cleeland and Squires (incorporated herein by reference, from within the Lorian text).

Preferred animal models include the neonatal mouse model, the rabbit cholera model and the tuberculosis mouse model. Another animal model, for treatment of a potentially lethal E. coli infection, is described in detail in Talley et al. U.S. Pat. No. 6,846,635, which description is hereby incorporated by reference for purposes of describing and enabling such an animal test.

The $ID_{50}/IC_{50}$ ratio required for safe use of the proposed inhibitor-antimicrobial peptide or combinations of peptide with other antimicrobial agents will be assessed by determining the $ID_{50}$ (median lethal toxic dosage) and the $IC_{50}$ (median effective therapeutic dosage) in experimental animals. The optimal dose for human subjects is then defined by fine-tuning the range in clinical trials. In the case of $DI_{50}$, the inhibitor is usually administered to mice or rats (orally or intraperitoneal) at several doses (usually 4-5) in the lethal rage. The dose in mg/kg is plotted against % mortality and the dose at 50% represents the $ID_{50}$. The $IC_{50}$ is determined in a similar fashion as described in the literature.

In a clinical trial, the therapeutic dose would be determined by maximizing the benefit to the patient, while minimizing any side effects or associated toxicities. Throughout the detailed examples, various therapeutic ranges are listed. Unless otherwise stated, these ranges refer to the amount of an agent to be administered orally.

In optimizing a therapeutic dose within the ranges disclosed herein, one would not use the upper limit of the range as the starting point in a clinical trial due to patient heterogeneity. Starting with a lower or mid-range dose level, and then increasing the dose will limit the possibility of eliciting a toxic or untoward reaction in any given patient or subset of patients. The presence of some side-effects or certain toxic reactions per se would not, of course, limit the utility of the invention, as it is well known that most beneficial drugs also produce a limited amount of undesirable effects in certain patients. Also, a variety of means are available to the skilled practitioner to counteract certain side effects, such as using vitamin B 12 in association with $N_2O$ treatment.

Zak and Sande (1981) reported on the correlation between the in vitro and in vivo activity of 1000 compounds that were randomly screened for antimicrobial activity. The important finding in this study is that negative in vitro data is particularly accurate, with the negative in vitro results showing more than a 99% correlation with negative in vivo activity. This is meaningful in the context of the present invention as one or more in vitro assays will be conducted prior to using any given combination in a clinical setting. Any negative result obtained in such an assay will thus be of value, allowing efforts to be more usefully directed.

In the treatment of animals or human patients with combination therapy, there are various appropriate formulations and treatment regimens that may be used. For example, the antimicrobial peptide and second agent(s) may be administered to an animal simultaneously, e.g., in the form of a single composition that includes the antimicrobial peptide and second agent, or by using at least two distinct compositions. The antimicrobial agent could also be administered to the animal prior to the second agent or the second agent may be given prior to the antimicrobial peptide.

Multiple combinations may also be used, such as more than one antimicrobial peptide used with one second agent or more than one second agent. Different classes of second agents and antimicrobial peptides may be combined, naturally following the general guidelines known in the art regarding drug interactions. Typically, between one and about five distinct antimicrobial agents are contemplated for use along with between one and about six antimicrobial peptides.

Further guidance on dosages and formulations is given in McCray et al. U.S. Pat. No. 6,809,181.

The peptides may also be incorporated into polymers, such as polysaccharides (cellulose, cellulose derivatives, starch, pectins, alginate, chitin, guar, carrageenan), glycol polymers, polyesters, polyurethanes, polyacrylates, polyacrylonitrile, polyamides (e.g., nylons), polyolefins, polystyrenes, vinyl polymers, polypropylene, silks or biopolymers. The peptides may be conjugated to any polymeric material such as those with the following specified functionality: 1) carboxy acid, 2) amino group, 3) hydroxyl group and/or 4) haloalkyl group. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). Topical formulations may be prepared, and may be combined with skin penetration enhancers such as sodium lauryl sulfate, as described in Antimicrobial Agents and Chemotherapy, September 2000, p. 2263-2270, Vol. 44, No. 9. Such compositions will contain a therapeutically effective amount of the antimicrobial peptides, preferably in purified form, together with a suitable amount of carrier so as to provide the form for proper administration to the patient. The formulation should suit the mode of administration.

In Vitro Efficacy Data

Three preferred peptides G11.46, G12.21 and G14.15, discussed above, were further tested for antimicrobial efficacy under various conditions using the 10% FCS/DMEM assay as described under CFU assay. The incubation times with the bacteria and peptide was three hours, at which time the bacteria were diluted and plated on agar. The superior performance of the peptides, discussed below, was generally noticeable at times earlier than 3 hrs. as well. The cfu/well are given in Tables 5 to 9 below. Table 5 shows activity of the three peptides against *B. cereus*, as well as the efficacy of vancomycin under similar conditions. The MIC for each compound is highlighted.

TABLE 5

| *B. Cereus* in 10% FCS/DMEM Media Time = 0 hr 9828 cfu/well | Time = 3 hrs 54481 cfu/well % Survival (CFU Assay) |
|---|---|
| Vancomycin (uM) | |
| 2.5 | 1.09 |
| 1.25 | 9.06 |
| 0.63 | 63.73 |
| 0.32 | 79.59 |
| 0.16 | 113.37 |
| 0.08 | 97.67 |
| G11.46 (uM) | |
| 0.16 | 0.002 |
| 0.08 | 0.002 |
| 0.04 | 0.02 |
| 0.02 | <0.5 |
| 0.01 | 44.62 |
| 0.005 | 103.49 |
| G12.21 (uM) | |
| 0.16 | 0.009 |
| 0.08 | 0.007 |
| 0.04 | 0.01 |
| 0.02 | 0.015 |
| 0.01 | 86.54 |
| 0.005 | 70.17 |
| G14.15 (μM) | |
| 0.16 | 0.01 |
| 0.08 | 34.21 |
| 0.04 | 82.56 |
| 0.02 | 103.92 |
| 0.01 | 104.56 |
| 0.005 | 102.53 |

The above Table 5 shows that the three peptides are 1-2 logs more effective than vancomycin in killing *B. cereus*.

Table 6 shows activity of the three peptides against *Staphylococcus aureus*.

TABLE 6

| Staph A in 10% FCS/DMEM Media Time = 0 hr 7988 cfu/well | Time = 3 hrs 44604 cfu/well % Survival (CFU Assay) |
|---|---|
| Gentamicin (µM) | |
| >1.25 | 17.1 |
| 0.63 | 28.51 |
| 0.32 | 37 |
| 0.16 | 59.49 |
| 0.08 | 78.94 |
| 0.04 | 90.73 |
| G11.46 (µM) | |
| 0.16 | 0.02 |
| 0.08 | 0.2 |
| 0.04 | 0.84 |
| 0.02 | 2.3 |
| 0.01 | 8.04 |
| 0.005 | 19.9 |
| G12.21 (µM) | |
| 0.63 | 0.99 |
| 0.32 | 1.55 |
| 0.16 | 5.07 |
| 0.08 | 9.15 |
| 0.04 | 16.86 |
| 0.02 | 22.7 |
| G14.15 (µM) | |
| 2.5 | 3.74 |
| 1.25 | 6.47 |
| 0.63 | 9.75 |
| 0.32 | 14.69 |
| 0.16 | 18.47 |
| 0.08 | 21.16 |

Table 6 shows that the three peptides tested compare favorably to gentamicin in killing *Staph*. A.

Table 7 below shows the activity of the three peptides against *Salmonella typhimurium*.

TABLE 7

| *Salmonella* in 10% FCS/DMEM | |
|---|---|
| Media Time = 0 hr 4838 cfu/well | Time = 3 hrs 44604 cfu/well % Survival (CFU Assay) |
| Gentamicin (µM) | |
| >1.25 | 29.7 |
| 0.63 | 70.15 |
| 0.32 | 93.27 |
| 0.16 | 105.73 |
| 0.08 | 103.72 |
| 0.04 | 119.73 |
| G11.46 (µM) | |
| 2.5 | <0.002 |
| 1.25 | 0.03 |
| 0.63 | 1.45 |
| 0.32 | 24.68 |
| 0.16 | 71.35 |
| 0.08 | 105 |
| 0.04 | 126.32 |
| 0.02 | 116.09 |
| G12.21 (µM) | |
| 5 | <0.002 |
| 2.5 | <0.002 |
| 1.25 | 0.81 |
| 0.63 | 8.4 |
| 0.32 | 30 |
| 0.16 | 68.46 |
| 0.08 | 100.32 |
| 0.04 | 105.96 |
| G14.15 (µM) | |
| 5 | <0.002 |
| 2.5 | 0.14 |
| 1.25 | 13.7 |
| 0.63 | 53.33 |
| 0.32 | 99.88 |
| 0.16 | 113.55 |
| 0.08 | 116.75 |
| 0.04 | 105.13 |

Table 7 shows that the three peptides compare favorably to gentamicin in killing *Salmonella*.

Table 8 below shows the activity of the three peptides against *E. coli*.

TABLE 8

| *E. Coli* in 10% FCS/DMEM Media Time = 0 hr 9923 cfu/well | Time = 3 hrs 63447 cfu/well % Survival (CFU Assay) |
|---|---|
| Gentamicin (µM) | |
| 2.5 | 0.052 |
| 1.25 | 0.21 |
| 0.63 | 17.05 |
| 0.32 | 87.76 |
| 0.16 | 110.6 |
| 0.08 | 117.89 |
| G11.46 (µM) | |
| 1.25 | <0.002 |
| 0.63 | <0.002 |
| 0.32 | 2.02 |
| 0.16 | 31.77 |
| 0.08 | 89.24 |
| 0.04 | 132.25 |
| 0.02 | 166.22 |
| 0.01 | 98.89 |
| G12.21 (µM) | |
| 1.25 | <0.002 |
| 0.63 | 0.86 |
| 0.32 | 12.17 |
| 0.16 | 33.49 |
| 0.08 | 76.98 |
| 0.04 | 106.59 |
| 0.02 | 153.1 |
| 0.01 | 108.53 |
| G14.15 (µM) | |
| 5 | <0.002 |
| 2.5 | 0.005 |
| 1.25 | 0.26 |
| 0.63 | 3.19 |
| 0.32 | 11.63 |
| 0.16 | 38.34 |
| 0.08 | 75.41 |
| 0.04 | 68.95 |
| 0.02 | 85.17 |

Table 8 shows that the three peptides compare favorably to gentamicin in killing *E. coli*.

Table 9 below repeats some data presented above in Tables 6, 7, and 8. It identifies the specific bacterial strains tested and shows The MIC for each compound/bacteria.

TABLE 9

| | CFU Assay in 10% FCS/DMEM (3 hrs) | | MIC (µM) | | |
|---|---|---|---|---|---|
| | Gentamicin | Vancomycin | G11.46 | G12.21 | G14.15 |
| E. Coli (ATCC#25922) | 1.25 | ND | 0.32-0.63 | 0.63 | 0.63-1.25 |
| Salmonella (SL1344) | 2.5-5 | ND | 0.63-1.25 | 1.25-2.5 | 2.5-5 |
| B. Cereus (ATCC#53522) | | 2.5 | 0.02 | 0.02 | 0.16 |
| Staph A (ATCC#29213) | >1.25 | >10 | 0.04-0.08 | 0.32-0.63 | 10 |

Table 9 above shows that the three peptides tested all performed at least as well as, if not better than, commonly used antibiotics for the strains tested. This performance would of course be vastly superior in cases where the bacterial strains were antibiotic resistant.

In addition to the data given above, the susceptibility of a panel of antibiotic resistant bacteria obtained from clinical isolates was tested. All of these are killed by the G11.46, G12.21, and G14.15 in DMEM with or without serum.

In Vivo Efficacy Data

G12.21 was tested in a mouse model for *Vibrio cholerae*. This gram negative pathogen is the most common bacteria in surface waters worldwide. When this infection becomes symptomatic, it can cause 25%-50% mortality in untreated patients.

In the present protocol, *V. cholerae* were obtained from an overnight culture of LB (Luria Broth), washed twice in 10 mM PBS, concentrated to $10^5$ cfu/5 µl in PBS and 0.03% LB. This preparation was administered to 4-5 day old Balb/c mice by placing 5 µl on the back of their throat with a pipette. After 3 hours, one group received 40 µl of 10 mM PBS and 0.03% LB by gavage and a second group received 25 µg of peptide in 40 µl by gavage. The mice were kept overnight at 30° C., sacrificed, and the large and small intestines were removed, processed in 5 ml PBS, and plated on LB/rifampicin plates overnight, and the resulting colonies counted. The results for *V. cholerae* are shown in FIG. 2.

Referring now to FIG. 2, the control group and 25 µg G12.21 group are compared, and it can be seen that the G12.21 group had significantly less *V. cholerae* colony forming units in both experiments shown (left panel and right panel).

In addition, *Staphylococcus aureus* was tested in a mouse model against peptides G11.46, G12.21, and G11.46 and 12.21 combined. *S. aureus* causes serious infections in humans, but these infections usually remain localized to the portal of entry by the human host defenses. *S. aureus* is a frequently acquired infection in hospitals (nosocomial infection), and hospital strains of *S. aureus* are usually resistant to a variety of different antibiotics. A few strains are resistant to all clinically useful antibiotics except vancomycin, and vancomycin-resistant strains are being increasingly reported. The term "MRSA" refers to Methicillin resistant *Staphylococcus aureus*. Methicillin resistance is widespread and most methicillin-resistant strains are also multiply resistant. *S. aureus* exhibits resistance to antiseptics and disinfectants, such as quaternary ammonium compounds, which may aid its survival in the hospital environment. Vancomycin and teicoplanin are glycopeptide antibiotics used to treat MRSA infections. Teicoplain is a structural congener of vancomycin that has a similar activity spectrum but a longer half-life (t½). Both drugs have low oral absorption thus are administered intravenously for systemic infections. Several new strains of MRSA have been found showing antibiotic resistance even to vancomycin and teicoplanin; those new evolutions of the MRSA bacteria are dubbed "vancomycin intermediate-resistant *Staphylococcus aureus*" (VISA).

In this protocol, BALB/c mice of 4-6 weeks of age were exposed to wounds on their backs, then inoculated with an infection of *S. aureus*, which had $10^5$ cfu per pocket ($2 \times 10^7$ cfu/µml DMEM) The *S. aureus* had been transfected with a plasmid containing luciferase as well as the substrate for luciferase. Using a special camera, light is detected from living bacteria in the wound. The light intensity is converted to a color scale. Controls received no peptide, and the treatment group received peptide at the indicated dose. Animals were imaged at 1, 3, 6 and 24 hrs. In each case, the treated wound showed significantly less infectivity. Representative data are summarized in FIG. 3.

Figure 3:
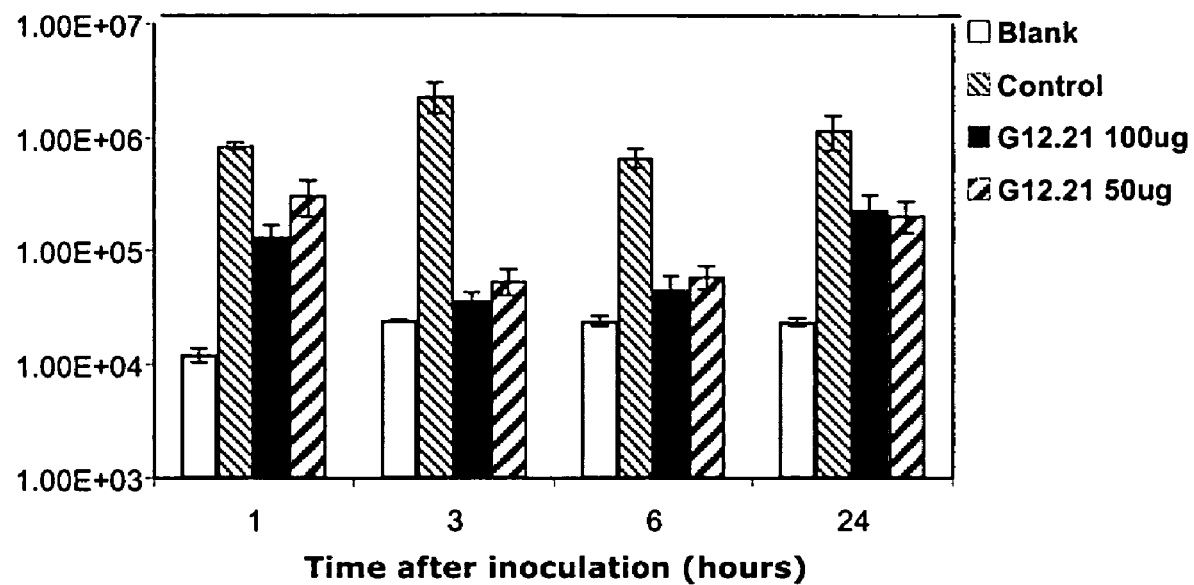
FIG. 3 is a bar graph showing the effect of different concentrations of G12.21 on *S. aureus* infection in vivo.

As shown in FIG. 3, G12.21 at both 100 µg (solid bar) and 50 µg (thick diagonal striped bar) showed significant reduction in light units compared to a control with no peptide although there is some recovery of bacteria by 24 hours. The "blank" represents an animal that did not receive any luminescent bacteria, but measures the small level of autoluminescence. The administration of G11.46 also resulted in significant reduction in light units in a similar experiment (data not shown), at 25 µg and 100 µg, although there is some recovery of bacteria by 24 hours. At 100 µg, after 6 hrs., light units approached levels obtained with the blank. The administration of a mixture of G21.21 and G11.46 (each at 50 µg) completely eradicated the bacteria even at 24 hours post injection, as shown in FIG. 4.

Finally, G12.21, G11.46 and G14.15 were shown to be active against *candida albicans* SC5314 at 10 nM phosphate buffer, 37° C., 90 min. incubation. These data are shown in FIG. 5, which represents the percentage of candida that survive treatment with peptide. In other experiments, peptide G12.21 killed *C. albicans* when cultured in RPMI 1640, and prevented the formation of germ tubes by the *Candida* at concentration as low as 0.03 µM peptide. Germ tube formation is essential to *Candida* toxicity, so agents that prevent this (even in the absence of killing the organism) could have significant activity in vivo.

Modified Amine Residues

Peptides of the present invention may comprise residues from any of the naturally-occurring amino acids, or from non-naturally-occurring amino acids. These naturally-occurring and non-naturally-occurring amino acids may be in the D or L configuration. The terms D and L are used herein as they are known to be used in the art. Peptides of the invention include single amino acids and short spans (e.g., 1-10) of amino acids. In addition, modified peptides of the present invention may also comprise a monomer or dimer.

The amino acids of the peptides of the present invention may also be modified. For example, amino groups may be acylated, alkylated or arylated. Benzyl groups may be halogenated, nitrosylated, alkylated, sulfonated or acylated.

Various chemically modified amino acids may be incorporated into the present peptides. Examples of these include:

Acetylated

N-acetyl-L-alanine, N-acetyl-L-arginine; N-acetyl-L-asparagine; N-acetyl-L-aspartic acid; N-acetyl-L-cysteine; N-acetyl-L-glutamine; N-acetyl-L-glutamic acid; N-acetylglycine; N-acetyl-L-histidine; N-acetyl-L-isoleucine; N-acetyl-L-leucine; N2-acetyl-L-lysine; N6-acetyl-L-lysine; N-acetyl-L-methionine; N-acetyl-L-phenylalanine; N-acetyl-L-proline; N-acetyl-L-serine; N-acetyl-L-threonine; N-acetyl-L-tryptophan; N-acetyl-L-tyrosine; N-acetyl-L-valine.

Amidated

L-alanine amide, L-arginine amide

Formylated

N-formyl-L-methionine

Hydroxylated 4-hydroxy-L-proline

Lipid Modified

S-farnesyl-L-cysteine, S-geranylgeranyl-L-cysteine, N-palmitoyl-L-cysteine, S-palmitoyl-L-cysteine, N-myristoyl-glycine, N6-myristoyl-L-lysine Methylated N-methyl-L-alanine, N,N,N-trimethyl-L-alanine, omega-N, omega-N-dimethyl-L-arginine, L-beta-methylthioaspartic acid, N5-methyl-L-glutamine, L-glutamic acid 5-methyl ester, 3'-methyl-L-histidine, N6-methyl-L-lysine, N6,N6-dimethyl-L-lysine, N6,N6,N6-trimethyl-L-lysine, N-methyl-L-methionine, N-methyl-L-phenylalanine.

Phosphorylated omega-N-phospho-L-arginine, L-aspartic 4-phosphoric anhydride, S-phospho-L-cysteine, 1'-phospho-L-histidine, 3'-phospho-L-histidine, O-phospho-L-serine, O-phospho-L-threonine, 04'-phospho-L-tyrosine Other L-selenocysteine, L-selenomethionine, L-3-oxoalanine, 2-pyrrolidone-5-carboxylic acid, L-glutamyl 5-glycerylphosphorylethanolamine, 2'-[3-carboxamido-3-(trimethylammonio)propyl]-L-histidine (diphthamide), N6-biotinyl-L-lysine, N6-(4-amino-2-hydroxybutyl)-L-lysine (hypusine), N6-retinal-L-lysine Other chemical modifications to the amino acids contained in the present peptides are known in the art, and described, for example in Kuhner et al. U.S. Pat. No. 6,858,581, which describes chemically modified antimicrobial peptides.

Nucleic Acids Encoding Antimicrobial Peptides

As used in this application, the term "an isolated nucleic acid encoding a antimicrobial peptide refers to a nucleic acid molecule that has been isolated free of total cellular nucleic acid. The term "functionally equivalent codon" is used herein to refer to codons that encode the same amino acid, such as the six codons for arginine or serine (Table 10, below), and also refers to codons that encode biologically equivalent amino acids, as discussed in the following pages.

TABLE 10

| Amino Acids | Codons |
| --- | --- |
| Alanine | GCA GCC GCG GCU |
| Cysteine | UGC UGU |
| Aspartic acid | GAC GAU |
| Glutamic acid | GAA GAG |
| Phenylalanine | UUC UUU |
| Glycine | GGA GGC GGG GGU |
| Histidine | CAC CAU |
| Isoleucine | AUA AUC AUU |
| Lysine | AAA AAG |
| Leucine | UUA UUG CUA CUC CUG CUU |
| Methionine | AUG |
| Asparagine | AAC AAU |
| Proline | CCA CCC CCG CCU |
| Glutamine | CAA CAG |
| Arginine | AGA AGG CGA CGC CGG CGU |
| Serine | AGC AGU UCA UCC UCG UCU |
| Threonine | ACA ACC ACG ACU |
| Valine | GUA GUC GUG GUU |
| Tryptophan | UGG |
| Tyrosine | UAC UAU |

As is known in the art, nucleic acids may be prepared and used to express the present peptides in cells, rather than preparing the peptides by chemical synthesis. Also, the present peptides may be administered in the form of DNA to be expressed in injected tissue, as described, for example in Bertoni et al. "Enhancement of plasmid-mediated gene therapy for muscular dystrophy by directed plasmid integration," PNAS, Jan. 10, 2006; 103(2): 419-424; M. Relloso and P. Esponda, "In-vivo transfection of the female reproductive tract epithelium," Mol. Hum. Reprod., Dec. 1, 2000; 6(12): 1099-1105. The peptide-encoding DNA may be administered by a viral vector, as described in Auricchio et al., "Noninvasive gene transfer to the lung for systemic delivery of therapeutic proteins," J Clin Invest. 2002 August; 110(4):499-504 and U.S. Pat. No. 6,696,423 to Barsoum, et al., issued Feb. 24, 2004, entitled "Methods and compositions for therapies using genes encoding secreted proteins such as interferon-beta," hereby incorporated by reference, and describing methods and pharmaceutical compositions for modifying cells of a mammalian recipient with DNA encoding a secreted protein such as human interferon in situ, which methods may be adapted to DNA encoding one of the present peptides.

CONCLUSION

The present examples, methods, procedures, specific compounds and molecules are meant to exemplify and illustrate the invention and should in no way be seen as limiting the scope of the invention, which is defined by the appended claims. Any patents or publications mentioned in this specification are indicative of levels of those skilled in the art to which the patent pertains and are hereby incorporated by reference to the same extent as if each was specifically and individually incorporated by reference and for the purpose of describing and enabling the method or material referred to.

What is claimed is:

1. An artificial antimicrobial peptide having:
   at least 90% sequence identity to peptide G11.46 (SEQ ID NO: 93), G12.21 (SEQ ID NO: 64) or G14.15 (SEQ ID NO: 83), but further having at least one non-identical amino acid when compared to SEQ ID NO: 2, an MIC against at least one of a pathogenic bacterium selected from the group consisting of *E. coli, S. typhimurium* and *B. cereus* of less than 10 µM; and
   having minimal lytic activity against mammalian cells.

2. The artificial antimicrobial peptide of claim 1 further comprised in a pharmaceutically acceptable composition.

3. The pharmaceutical preparation of claim 2 further comprising a sterile lyophilized powder.

4. The artificial antimicrobial peptide of claim 1 having a net positive charge of at least 8.

5. The artificial peptide of claim 1 having more D-amino acids than L-amino acids.

6. The artificial peptide of claim 1 having at least 3 hydrophobic residues.

7. An artificial antimicrobial peptide selected from the group consisting of:

G8.17, (SEQ ID NO: 9), G8.3, (SEQ ID NO: 12), G8.15, (SEQ ID NO: 13), G8.11, (SEQ ID NO: 18), G11.6, (SEQ ID NO: 16), G11.3, (SEQ ID NO: 26), G11.24, (SEQ ID NO: 26), G11.30, (SEQ ID NO: 39), G11.32, (SEQ ID NO: 41), G11.34, (SEQ ID NO: 26), G11.35, (SEQ ID NO: 48), G11.55, (SEQ ID NO: 35), G11.46, (SEQ ID NO: 93), G12.5, (SEQ ID NO: 51), G12.10, (SEQ ID NO: 61), G12.19, (SEQ ID NO: 65), G12.20, (SEQ ID NO: 66), G12.21, (SEQ ID NO: 64), G14.2, (SEQ ID NO: 81), G14.10, (SEQ ID NO: 81), G14.11, (SEQ ID NO: 83), and G14.15 (SEQ ID NO: 83), wherein said peptide has an MIC (μM) in at least two microbial organisms selected from the group consisting of: *E. coli, S. typhimurium, V. cholerae* and *B. cereus* of less than about 2.0, and further has minimal lysis of mammalian cells.

8. The peptide of claim 7 wherein said peptide is selected from: G8.3, (SEQ ID NO: 12), G8.15, (SEQ ID NO: 13), G 8.11, (SEQ ID NO: 18), G11.46, (SEQ ID NO: 93), G12.21 (SEQ ID NO: 64), and G14.15 (SEQ ID NO: 83).

9. The peptide of claim 7 selected from the group consisting of G11.46, (SEQ ID NO: 93), G12.21 (SEQ ID NO: 64), and G14.15 (SEQ ID NO: 83).

10. The peptide of claim 7 comprising at least 50% D-amino acids.

11. The peptide of claim 7 comprising the sequence arg-arg-val-ser-arg-arg (SEQ ID NO: 92).

12. The peptide of claim 7 comprising at least 50% D-amino acids.

13. The peptide of claim 7 comprising the sequence arg-arg-val-ser-arg-arg (SEQ ID NO: 92).

14. A method of inhibiting microbial growth in an infected subject, comprising administering to said subject a composition comprising a peptide having a formula according to claim 7.

15. A method of inhibiting microbial growth in an infected subject, comprising administering to said subject a composition comprising a peptide having a formula according to claim 4.

16. A method for treating bacterial or fungal infection, comprising administering to a living body in need of such treatment a therapeutically effective amount of a peptide according to claim 1.

17. A method for preparing an antimicrobial peptide, comprising:

(a) selecting a sequence of between 10 and 20 residues comprised in SEQ ID NO: 2;

(b) modifying the sequence by increasing a selected number of charged residues to be at least 8 residues;

(c) modifying the sequence to include at least one D-amino acid;

(d) preparing the peptide;

(e) testing the peptide for antimicrobial activity against at least 3 microorganisms and selecting only a peptide with an MIC less than 1.0 μM against at least one of the microorganisms, and selecting as the antimicrobial peptide one having at least 90% sequence identity to peptide G11.46, (SEQ ID NO: 93), G12.21 (SEQ ID NO: 64), or 90% sequence identity to G14.15 (SEQ ID NO: 83), having at least one non-identical amino acid when compared to SEQ ID NO: 2 and having minimum lytic activity against mammalian cells.

18. The method of claim 17 further comprising the step of preparing a dendrimer containing the peptide.

19. The method of claim 17 further comprising the step of including at least one chemically modified amino acid.

20. The peptide of claim 1 further comprised in a dendrimer.

21. The peptide of claim 1 comprising at least 7 arg residues.

22. The peptide of claim 1 further comprising at least one chemically modified amino acid.

23. The peptide of claim 1 wherein the MIC against at least one of a pathogenic bacterium is less than 1 μM.

* * * * *

UNITED STATES PATENT AND TRADEMARK OFFICE
CERTIFICATE OF CORRECTION

| | | |
|---|---|---|
| PATENT NO. | : 7,745,390 B2 | Page 1 of 1 |
| APPLICATION NO. | : 11/438563 | |
| DATED | : June 29, 2010 | |
| INVENTOR(S) | : Clayberger et al. | |

It is certified that error appears in the above-identified patent and that said Letters Patent is hereby corrected as shown below:

In the Specification Under Column 1:

• Please replace Column 1, line no. 10-15 with:

-- FEDERALLY-SPONSORED RESEARCH OR DEVELOPMENT
This invention was made with Government support under contracts AI056548 and AI043348 awarded by the National Institutes of Health. The Government has certain rights in this invention. --

Signed and Sealed this
Twenty-third Day of April, 2013

Teresa Stanek Rea
*Acting Director of the United States Patent and Trademark Office*

SEQUENCE LISTING

<160> NUMBER OF SEQ ID NOS: 93

<210> SEQ ID NO 1
<211> LENGTH: 172
<212> TYPE: PRT
<213> ORGANISM: Homo sapiens

<400> SEQUENCE: 1

Met Ala Thr Trp Ala Leu Leu Leu Ala Ala Met Leu Leu Gly Asn
1               5                   10                  15

Pro Gly Leu Glu Val Ser Val Ser Pro Lys Gly Lys Asn Thr Ser Gly
            20                  25                  30

Arg Glu Ser Gly Phe Gly Trp Ala Ile Trp Met Glu Gly Leu Val Phe
            35                  40                  45

Ser Arg Leu Ser Pro Glu Tyr Tyr Asp Leu Ala Arg Ala His Leu Arg
        50                  55                  60

Asp Glu Glu Lys Ser Cys Pro Cys Leu Ala Gln Gly Pro Gln Gly
65                  70                  75                  80

Asp Leu Leu Thr Lys Thr Gln Glu Leu Gly Arg Asp Tyr Arg Thr Cys
                85                  90                  95

Leu Thr Ile Val Gln Lys Leu Lys Lys Met Val Asp Lys Pro Thr Gln
            100                 105                 110

Arg Ser Val Ser Asn Ala Ala Thr Arg Val Cys Arg Thr Gly Arg Ser
            115                 120                 125

Arg Trp Arg Asp Val Cys Arg Asn Phe Met Arg Arg Tyr Gln Ser Arg
    130                 135                 140

Val Ile Gln Gly Leu Val Ala Gly Glu Thr Ala Gln Gln Ile Cys Glu
145                 150                 155                 160

Asp Leu Arg Leu Cys Ile Pro Ser Thr Gly Pro Leu
                165                 170

<210> SEQ ID NO 2
<211> LENGTH: 39
<212> TYPE: PRT
<213> ORGANISM: Homo sapiens

<400> SEQUENCE: 2

Gln Arg Ser Val Ser Asn Ala Ala Thr Arg Val Cys Arg Thr Gly Arg
1               5                   10                  15

Ser Arg Trp Arg Asp Val Cys Arg Asn Phe Met Arg Arg Tyr Gln Ser
            20                  25                  30

Arg Val Ile Gln Gly Leu Val
            35

<210> SEQ ID NO 3
<211> LENGTH: 14
<212> TYPE: PRT
<213> ORGANISM: Homo sapiens

<400> SEQUENCE: 3

Gln Arg Ser Val Ser Asn Ala Ala Thr Arg Val Cys Arg Thr
1               5                   10

<210> SEQ ID NO 4
<211> LENGTH: 5
<212> TYPE: PRT
<213> ORGANISM: Homo sapiens

```
<400> SEQUENCE: 4

Gly Arg Ser Arg Trp
 1               5

<210> SEQ ID NO 5
<211> LENGTH: 5
<212> TYPE: PRT
<213> ORGANISM: Homo sapiens

<400> SEQUENCE: 5

Gly Gln Ser Gln Trp
 1               5

<210> SEQ ID NO 6
<211> LENGTH: 10
<212> TYPE: PRT
<213> ORGANISM: Homo sapiens

<400> SEQUENCE: 6

Arg Asp Val Cys Arg Asn Phe Met Arg Arg
 1               5                  10

<210> SEQ ID NO 7
<211> LENGTH: 9
<212> TYPE: PRT
<213> ORGANISM: Homo sapiens

<400> SEQUENCE: 7

Gln Ser Arg Val Ile Gln Gly Leu Val
 1               5

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Arg Ser Val Ser Asn Ala Ala Thr Arg Val Cys Arg Thr Gly Arg
 1               5                  10                  15

Ser Arg Trp Arg Asp Val Cys Arg Asn Phe Met Arg Arg
                20                  25

<210> SEQ ID NO 9
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Arg Ser Val Ser Asn Ala Ala Thr Arg Val Ser Arg Thr Gly Arg
 1               5                  10                  15

Ser Arg Trp Arg Asp Val Ser Arg Asn Phe Met Arg Arg
                20                  25

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: Synthetic
```

```
                       peptide

<400> SEQUENCE: 10

Gln Arg Ser Val Ser Asn Pro Pro Thr Arg Val Ser Arg Pro Pro Arg
  1               5                  10                  15

Ser Arg Trp Arg Asp Val Ser Arg Pro Pro Met Arg Arg
             20                  25

<210> SEQ ID NO 11
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Arg Ser Val Ser Arg Ala Ala Thr Arg Val Ser Arg Thr Gly Arg
  1               5                  10                  15

Ser Arg Trp Arg Asp Val Ser Arg Asn Phe Met Arg Arg
             20                  25

<210> SEQ ID NO 12
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Arg Ser Val Ser Asn Ala Ala Thr Arg Val Ser Arg Thr Gly Arg
  1               5                  10                  15

Ser Arg Trp Arg Asp Val Ser Arg Arg Phe Met Arg Arg
             20                  25

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Arg Ser Val Ser Arg Ala Ala Thr Arg Val Ser Arg Thr Gly Arg
  1               5                  10                  15

Ser Asn Trp Arg Asp Val Gly Arg Arg Phe Met Arg Arg
             20                  25

<210> SEQ ID NO 14
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Arg Ser Val Ser Arg Ala Ala Thr Arg Val Ser Arg Thr Gly Arg
  1               5                  10                  15

Ser Arg Trp Arg Asp Val Ser Arg Arg Phe Met Arg Arg
             20                  25
```

```
<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Arg Ala Val Ala Arg Ala Ala Thr Arg Val Ala Arg Thr Gly Arg
 1               5                  10                  15

Ala Arg Trp Arg Asp Val Ala Arg Asn Phe Met Arg Arg
            20                  25

<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Arg Ala Val Ala Asn Ala Ala Thr Arg Val Ala Arg Thr Gly Arg
 1               5                  10                  15

Ala Arg Trp Arg Asp Val Ala Arg Arg Phe Met Arg Arg
            20                  25

<210> SEQ ID NO 17
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Arg Ala Val Ala Arg Ala Ala Thr Arg Val Ala Arg Thr Gly Arg
 1               5                  10                  15

Ala Arg Trp Arg Asp Val Ala Arg Arg Phe Met Arg Arg
            20                  25

<210> SEQ ID NO 18
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Arg Ser Val Ser Arg Pro Pro Thr Arg Val Ser Arg Thr Gly Arg
 1               5                  10                  15

Ser Arg Trp Arg Asp Val Ser Arg Arg Phe Met Arg Arg
            20                  25

<210> SEQ ID NO 19
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Arg Ser Val Ser Arg Ala Ala Thr Arg Val Ser Arg Thr Gly Arg
```

```
                1               5                  10                 15
Ser Arg Trp Arg Arg Val Ser Arg Arg Phe Met Arg Arg
                20                 25

<210> SEQ ID NO 20
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Arg Ala Val Ala Arg Ala Ala Thr Arg Val Ala Arg Thr Gly Arg
 1               5                  10                 15
Ala Arg Trp Arg Arg Val Ala Arg Arg Phe Met Arg Arg
                20                 25

<210> SEQ ID NO 21
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Trp Arg Asp Val Ser Arg Asn Phe Met Arg Arg Gly Arg Ser Arg Gly
 1               5                  10                 15
Trp Arg Asp Val Ser Arg Asn Phe Met Arg Arg
                20                 25

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Asp Val Ser Arg Arg Phe Met Arg Arg Gly Ser Arg Asp Val Ser
 1               5                  10                 15
Arg Arg Phe Met Arg Arg
                20

<210> SEQ ID NO 23
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Asp Val Ser Arg Arg Phe Met Arg Arg Gly Ser Arg Asp Val Ser
 1               5                  10                 15
Arg Arg Phe Met Arg Arg Gly Ser Arg Asp Val Ser Arg Arg Phe Met
                20                 25                 30
Arg Arg

<210> SEQ ID NO 24
<211> LENGTH: 21
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 24

Arg Asp Val Ser Arg Arg Phe Met Arg Arg Gly Asp Val Ser Arg
1               5                   10                  15

Arg Phe Met Arg Arg
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Asp Val Ser Arg Arg Phe Met Arg Arg Asp Val Ser Arg Arg
1               5                   10                  15

Phe Met Arg Arg
            20

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Arg Val Ser Arg Arg Phe Met Arg Arg
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Arg Val Val Arg Arg Phe Met Arg Arg
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: cyclohexyl-Gly

<400> SEQUENCE: 28

Arg Arg Val Xaa Arg Arg Phe Met Arg Arg
1               5                   10

<210> SEQ ID NO 29
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Arg Val Val Arg Arg Leu Leu Arg Arg
 1               5                  10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Arg Leu Leu Arg Arg Leu Leu Arg Arg
 1               5                  10

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Arg Leu Leu Arg Arg Leu Leu Arg Arg Gly Ser Arg Arg Leu Leu
 1               5                  10                  15

Arg Arg Leu Leu Arg Arg
            20

<210> SEQ ID NO 32
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Arg Val Ser Arg Arg Phe Met Arg Arg Gly Ser Arg Arg Val Ser
 1               5                  10                  15

Arg Arg Phe Met Arg Arg
            20

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Lys Val Ser Lys Lys Phe Met Lys Lys
 1               5                  10

<210> SEQ ID NO 34
<211> LENGTH: 22
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 34

Lys Lys Val Ser Lys Lys Phe Met Lys Lys Gly Ser Lys Lys Val Ser
 1               5                  10                  15

Lys Lys Phe Met Lys Lys
            20

<210> SEQ ID NO 35
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Lys Val Ser Lys Lys Phe Met Lys Lys Gly Ser Lys Lys Val Ser
 1               5                  10                  15

Lys Lys Phe Met Lys Lys Gly Ser Lys Lys Val Ser Lys Lys Phe Met
            20                  25                  30

Lys Lys

<210> SEQ ID NO 36
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Arg Val Ser Arg Arg Phe Met Arg Arg Gly Ser Arg Arg Val Ser
 1               5                  10                  15

Arg Arg Phe Met Arg Arg Gly Ser Arg Arg Val Ser Arg Arg Phe Met
            20                  25                  30

Arg Arg

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Arg Asp Ser Arg Arg Phe Met Arg Arg
 1               5                  10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Cys Arg Arg Val Ser Arg Arg Phe Met Arg Arg Cys
 1               5                  10

<210> SEQ ID NO 39
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Arg Val Ser Arg Arg Phe Met Arg Arg Asp
 1               5                  10

<210> SEQ ID NO 40
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Lys Lys Val Ser Lys Lys Phe Met Lys Lys Gly Ser Lys Lys Val
 1               5                  10                  15

Ser Lys Lys Phe Met Lys Lys Cys
             20

<210> SEQ ID NO 41
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Lys Val Ser Lys Lys Phe Met Lys Lys Gly Ser Lys Lys Val Ser
 1               5                  10                  15

Lys Lys Phe Met Lys Lys Asp
             20

<210> SEQ ID NO 42
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Arg Met Phe Arg Arg Ser Val Arg Arg Cys Cys Arg Arg Val Ser
 1               5                  10                  15

Arg Arg Phe Met Arg Arg
             20

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Arg Pro Ser Arg Arg Phe Pro Arg Arg
 1               5                  10

<210> SEQ ID NO 44
```

```
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Arg Val Ser Arg Arg Phe Met Arg Arg Ser Gly Ser Gly Ser Gly
 1               5                  10                  15

Ser Gly Gln Gln Met Val Gln Gln Ser Gly Gln Gln Phe Ser
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Arg Val Ser Arg Arg Phe Met Arg Arg Ser Arg Trp Ala Arg Lys
 1               5                  10                  15

Gly Ser Gly Gln Met Val Gln Gln Ser Ser Gln Gln Phe Gln
            20                  25                  30

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Val His Lys Arg Arg Val Ser Arg Arg Phe Met Arg Arg Leu Gly His
 1               5                  10                  15

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Phe Asp Thr Pro Arg Arg Val Ser Arg Arg Phe Met Arg Arg Leu Gly
 1               5                  10                  15

His

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Arg Val Ser Arg Arg Phe Met Arg Arg
 1               5                  10

<210> SEQ ID NO 49
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Asp Val Cys Arg Asn Phe Met Arg Arg Tyr Gln Ser Arg Val Ile
 1               5                  10                  15

Gln Gly Leu Val
            20

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Asp Val Ser Arg Asn Phe Met Arg Arg Tyr Gln Ser Arg Val Ile
 1               5                  10                  15

Gln Gly Leu Val
            20

<210> SEQ ID NO 51
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Asp Val Ser Arg Arg Phe Met Arg Arg Tyr Gln Ser Arg Val Ile
 1               5                  10                  15

Gln Gly Leu Val
            20

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Asp Val Ser Arg Arg Phe Met Arg Arg Gln Ser Arg Val Ile Gln
 1               5                  10                  15

Gly Leu Val

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Asp Val Ala Arg Arg Phe Met Arg Arg Gln Ser Arg Val Ile Ser
 1               5                  10                  15

Arg Leu Val
```

```
<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Asp Val Ala Arg Arg Phe Met Arg Arg Gln Ser Arg Val Ile Arg
 1               5                  10                  15

Arg Leu Val

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Asp Val Ala Lys Lys Phe Met Lys Lys Gln Ser Lys Val Ile Lys
 1               5                  10                  15

Lys Leu Val

<210> SEQ ID NO 56
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Asp Val Ala Arg Arg Phe Met Arg Arg Tyr Gln Ala Arg Val Ile
 1               5                  10                  15

Gln Gly Leu Val
            20

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Arg Val Ser Arg Arg Phe Met Arg Arg Tyr Gln Ser Arg Val Ile
 1               5                  10                  15

Gln Gly Leu Val
            20

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Arg Val Ser Arg Arg Phe Met Arg Arg Tyr Arg Ser Arg Val Ile
```

```
                1               5                   10                  15
Arg Gly Leu Val
            20

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Arg Val Ser Arg Arg Phe Met Arg Arg Tyr Arg Ser Arg Arg Ile
1               5                   10                  15
Arg Arg Leu Val
            20

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Lys Val Ser Lys Lys Phe Met Lys Lys Tyr Gln Ser Lys Val Ile
1               5                   10                  15
Gln Gly Leu Val
            20

<210> SEQ ID NO 61
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Arg Val Ser Arg Arg Phe Met Arg Arg Tyr Gln Ser Arg Val Pro
1               5                   10                  15
Gln Gly Leu Val
            20

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Arg Arg Ser Ser Arg Phe Met Arg Arg Tyr Gln Arg Val Val Pro
1               5                   10                  15
Arg Gly Leu Val
            20

<210> SEQ ID NO 63
<211> LENGTH: 20
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 63

Arg Arg Val Ser Arg Arg Phe Met Arg Tyr Arg Ser Arg Arg Pro
 1               5                  10                  15

Arg Arg Leu Val
            20

<210> SEQ ID NO 64
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Arg Val Ser Arg Arg Pro Met Arg Tyr Arg Ser Arg Arg Pro
 1               5                  10                  15

Arg Arg Leu Val
            20

<210> SEQ ID NO 65
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Arg Val Ser Arg Pro Pro Pro Arg Tyr Arg Ser Arg Arg Pro
 1               5                  10                  15

Arg Arg Leu Val
            20

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Arg Val Ser Arg Pro Pro Met Arg Tyr Arg Ser Arg Arg Pro
 1               5                  10                  15

Arg Arg Leu Val
            20

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Arg Ser Val Ser Asn Ala Ala Thr Arg Val Cys Arg Thr Gly Arg
 1               5                  10                  15

Ser Arg Trp

```
<210> SEQ ID NO 68
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Arg Ser Val Ser Asn Ala Ala Thr Arg Val Ser Arg Thr Gly Arg
 1               5                  10                  15

Ser Arg Trp

<210> SEQ ID NO 69
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Arg Ser Val Ser Arg Ala Ala Thr Arg Val Ser Arg Thr Gly Arg
 1               5                  10                  15

Ser Arg Trp

<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Arg Ser Val Ser Arg Pro Pro Thr Arg Val Ser Arg Pro Pro Arg
 1               5                  10                  15

Ser Arg Trp

<210> SEQ ID NO 71
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Arg Ala Val Ala Arg Ala Ala Thr Arg Val Ala Arg Thr Gly Arg
 1               5                  10                  15

Ala Arg Trp

<210> SEQ ID NO 72
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Arg Ser Val Ser Arg Ala Pro Thr Arg Val Ser Arg Thr Gly Arg
 1               5                  10                  15

Ser Arg Trp
```

```
<210> SEQ ID NO 73
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Lys Ser Val Ser Lys Ala Ala Thr Lys Val Ser Lys Thr Gly Lys
 1               5                  10                  15

Ser Lys Trp

<210> SEQ ID NO 74
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Arg Ser Val Ser Arg Pro Pro Thr Arg Val Ser Arg Thr Gly Arg
 1               5                  10                  15

Ser Arg Trp

<210> SEQ ID NO 75
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Arg Ser Val Ser Arg Pro Pro Thr Arg Val Ser Arg Thr Gly Arg
 1               5                  10                  15

Ala Arg Trp

<210> SEQ ID NO 76
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Arg Ser Val Ser Arg Ala Ala Thr Arg Val Cys Arg Thr Gly Arg
 1               5                  10                  15

Ser Asn Trp

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Arg Ser Arg Trp Arg Asp Val Cys Arg Asn Phe Met Arg Arg
 1               5                  10                  15
```

```
<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Arg Ser Arg Trp Arg Asp Val Ser Arg Asn Phe Met Arg Arg
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Arg Ser Gly Trp Arg Asp Val Ser Arg Asn Phe Arg Arg Gly
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Arg Ser Leu Trp Arg Asp Val Ser Arg Asn Phe Met Arg Arg
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Arg Ser Arg Trp Arg Asp Val Ser Arg Arg Phe Met Arg Arg
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Arg Ala Arg Trp Arg Asp Val Ala Arg Arg Phe Met Arg Arg
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83
```

```
Gly Arg Ser Arg Trp Arg Arg Val Ser Arg Arg Phe Met Arg Arg
 1               5                  10                  15

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Ser Arg Arg Trp Arg Asp Val Ser Arg Arg Phe Met Arg Arg
 1               5                  10                  15

<210> SEQ ID NO 85
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Arg Ser Arg Trp Arg Asp Val Ser Arg Asn Phe Met Arg Arg Tyr
 1               5                  10                  15

Gln Ser Arg Val Ile Gln Gly Leu Val
            20                  25

<210> SEQ ID NO 86
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Arg Ser Val Ser Asn Ala Ala Thr Arg Val Ser Arg Thr Gly Arg
 1               5                  10                  15

Ser Arg Trp Arg Asp Val Ser Arg Asn Phe Met Arg Arg Tyr Gln Ser
            20                  25                  30

Arg Val Ile Gln Gly Leu Val
            35

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Arg Ser Val Arg Arg Phe Met Arg Arg Asp
 1               5                  10

<210> SEQ ID NO 88
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88
```

```
Lys Lys Val Ser Lys Lys Phe Met Lys Lys Gly Ser Lys Lys Val Ser
 1               5                  10                  15

Lys Lys Phe Met Lys Lys Asp
            20
```

```
<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Arg Ser Val Arg Arg Phe Met Arg Arg
 1               5                  10
```

```
<210> SEQ ID NO 90
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Lys Lys Val Ser Lys Lys Phe Met Lys Lys Gly Ser Lys Lys Val Ser
 1               5                  10                  15

Lys Lys Phe Met Lys Lys
            20
```

```
<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Arg Val Ser Arg Arg Phe Met Arg Arg
 1               5                  10
```

```
<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Arg Arg Val Ser Arg Arg
 1               5
```

```
<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Arg Arg Arg Arg Arg Arg Val Ser Arg Arg Phe Met Arg Arg
 1               5                  10                  15
```